US008506569B2

(12) United States Patent
Keefer et al.

(10) Patent No.: US 8,506,569 B2
(45) Date of Patent: Aug. 13, 2013

(54) RECIPROCATING RASPS FOR USE IN AN ORTHOPAEDIC SURGICAL PROCEDURE

(75) Inventors: Ryan C. Keefer, Fort Wayne, IN (US); Sarah M. Anthony, Leesburg, IN (US); Conrad L. Klotz, Nappanee, IN (US); Kyle E. Lappin, Fort Wayne, IN (US); Van A. Flamion, Warsaw, IN (US); James A. Caywood, Fort Wayne, IN (US); Francisco A. Amaral, Acushnet, MA (US); Michael J. Fortin, Acushnet, MA (US); Gabriel M. Surma, Winona Lake, IN (US); Joanna L. Surma, Winona Lake, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 102 days.

(21) Appl. No.: 12/956,914

(22) Filed: Nov. 30, 2010

(65) Prior Publication Data

US 2011/0213372 A1 Sep. 1, 2011

Related U.S. Application Data

(60) Provisional application No. 61/291,455, filed on Dec. 31, 2009.

(51) Int. Cl.
*A61B 17/16* (2006.01)
*A61B 17/14* (2006.01)
*A61B 17/32* (2006.01)

(52) U.S. Cl.
USPC ............... 606/85; 636/80; 636/81; 636/167; 636/171; 636/177

(58) Field of Classification Search
USPC ............... 606/79–81, 84, 85, 167, 170, 171, 606/177; 407/29.1, 29.14, 65; 451/179, 451/358, 359
See application file for complete search history.

(56) References Cited

U.S. PATENT DOCUMENTS

| 166,868 A | 8/1875 | Haptonstall |
|---|---|---|
| 472,259 A | 4/1892 | Goodell et al. |

(Continued)

FOREIGN PATENT DOCUMENTS

| EP | 0378002 B1 | 12/1993 |
|---|---|---|
| EP | 0903127 A2 | 3/1999 |

(Continued)

OTHER PUBLICATIONS

Extended European Search Report, European Patent Application No. 10196415.3-2310, Apr. 21, 2011, 7 pages.

(Continued)

*Primary Examiner* — Kevin T Truong
*Assistant Examiner* — Tracy Kamikawa
(74) *Attorney, Agent, or Firm* — Barnes & Thornburg LLP

(57) ABSTRACT

Reciprocating rasps for the surgical preparation of the bone prior to the implantation of a glenoid or acetabular component with complex geometry are disclosed. Surgical methods for the use of such reciprocating rasps are also disclosed. A reciprocating rasp for use in the surgical preparation of an acetabulum includes a shaft having a first end configured to be secured in a chuck of a reciprocating tool, and a cutting head secured to a second end of the shaft. The cutting head includes a cutting surface having a plurality of cutting teeth arranged in a geometry that corresponds with a geometry of the acetabular component, and an alignment guide that is devoid of cutting teeth and configured to cooperate with a complementary alignment guide of an acetabular trial instrument when the cutting head is secured to the second end of the shaft.

3 Claims, 33 Drawing Sheets

(56) References Cited

U.S. PATENT DOCUMENTS

| | | | |
|---|---|---|---|
| 1,042,728 A | 10/1912 | Vernaz | |
| 4,625,725 A | 12/1986 | Davison et al. | |
| 4,865,605 A | 9/1989 | Dines et al. | |
| 5,169,401 A | 12/1992 | Lester et al. | |
| 5,282,865 A | 2/1994 | Dong | |
| 5,403,318 A | 4/1995 | Boehringer et al. | |
| 5,553,476 A | 9/1996 | Oehy et al. | |
| 6,022,353 A | 2/2000 | Fletcher et al. | |
| 6,245,074 B1 * | 6/2001 | Allard et al. | 606/80 |
| 6,503,253 B1 | 1/2003 | Fletcher et al. | |
| 6,699,289 B2 | 3/2004 | Iannotti et al. | |
| 6,723,101 B2 | 4/2004 | Fletcher et al. | |
| 6,780,190 B2 | 8/2004 | Maroney | |
| 6,884,246 B1 | 4/2005 | Sonnabend et al. | |
| 6,911,047 B2 | 6/2005 | Rockwood, Jr. et al. | |
| 7,160,328 B2 | 1/2007 | Rockwood, Jr. et al. | |
| 7,220,264 B1 * | 5/2007 | Hershberger | 606/81 |
| 7,329,284 B2 | 2/2008 | Maroney et al. | |
| 7,527,628 B2 | 5/2009 | Fletcher et al. | |
| 7,572,259 B2 * | 8/2009 | Desarzens et al. | 606/81 |
| 7,611,516 B2 | 11/2009 | Maroney | |
| 7,621,915 B2 * | 11/2009 | Frederick et al. | 606/80 |
| 7,901,424 B2 | 3/2011 | Fletcher et al. | |
| 7,909,828 B2 * | 3/2011 | Fehlbaum et al. | 606/81 |
| 8,052,689 B2 * | 11/2011 | Sherry et al. | 606/81 |
| 2002/0099381 A1 | 7/2002 | Maroney | |
| 2002/0099445 A1 | 7/2002 | Maroney et al. | |
| 2004/0034431 A1 | 2/2004 | Maroney et al. | |
| 2004/0243134 A1 | 12/2004 | Walker et al. | |
| 2005/0021038 A1 | 1/2005 | Maroney | |
| 2005/0043805 A1 | 2/2005 | Chudik | |
| 2005/0192583 A1 | 9/2005 | Walker et al. | |
| 2005/0192584 A1 | 9/2005 | Walker et al. | |
| 2005/0234463 A1 | 10/2005 | Hershberger et al. | |
| 2005/0288676 A1 | 12/2005 | Schnieders et al. | |
| 2006/0009776 A1 | 1/2006 | Justin et al. | |
| 2006/0195194 A1 | 8/2006 | Gunther | |
| 2007/0092841 A1 | 4/2007 | Kawashima | |
| 2007/0198002 A1 | 8/2007 | Melsheimer et al. | |
| 2007/0219637 A1 | 9/2007 | Berelsman et al. | |
| 2007/0233131 A1 | 10/2007 | Song et al. | |
| 2007/0293868 A1 | 12/2007 | Delfosse et al. | |
| 2008/0003066 A1 | 1/2008 | Haugaard | |
| 2008/0147075 A1 | 6/2008 | Bonutti | |
| 2008/0275453 A1 | 11/2008 | Lafosse et al. | |
| 2009/0093815 A1 | 4/2009 | Fletcher et al. | |
| 2010/0249938 A1 | 9/2010 | Gunther et al. | |

FOREIGN PATENT DOCUMENTS

| | | |
|---|---|---|
| EP | 1224912 A2 | 7/2002 |
| EP | 1550419 A2 | 7/2005 |
| EP | 1764046 A2 | 3/2007 |
| WO | 0134040 A1 | 5/2001 |
| WO | 2004108012 A2 | 12/2004 |
| WO | 2006078511 A1 | 7/2006 |
| WO | 2006078864 A1 | 7/2006 |
| WO | 2006136955 A1 | 12/2006 |
| WO | 2008005941 A2 | 1/2008 |
| WO | 2009111639 A1 | 9/2009 |
| WO | 2010033473 A2 | 3/2010 |

OTHER PUBLICATIONS

Extended European Search Report, European Patent Application No. 10196412.0-2310, Apr. 20, 2011, 7 pages.

European Search Report, European Patent Application No. 12151782.5-2310, May 7, 2012, 6 pages.

Global AP Adjustable Prosthesis, Surgical Technique, Copyright 2009, 64 pages.

Delta Xtend Reverse Shoulder System, Design Rationale and Surgical Technique, Copyright 2009, 64 pages.

* cited by examiner

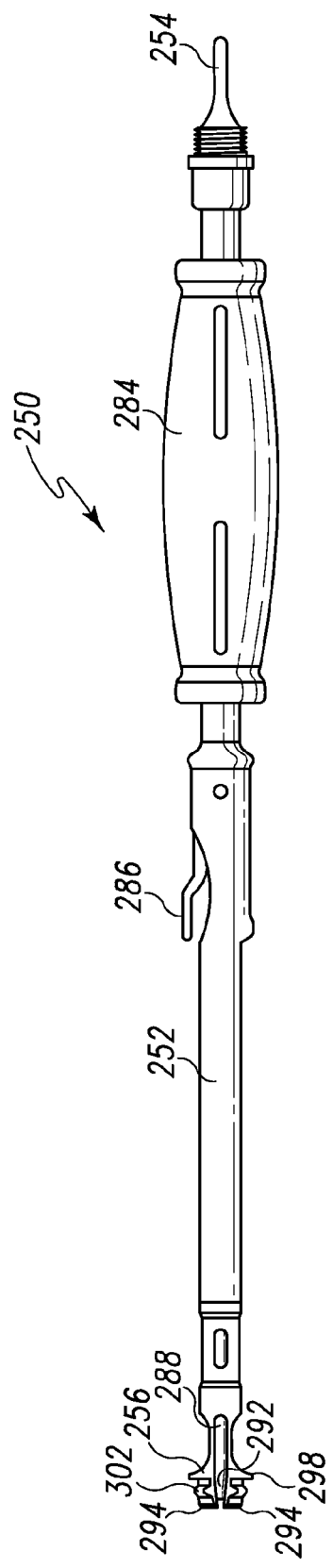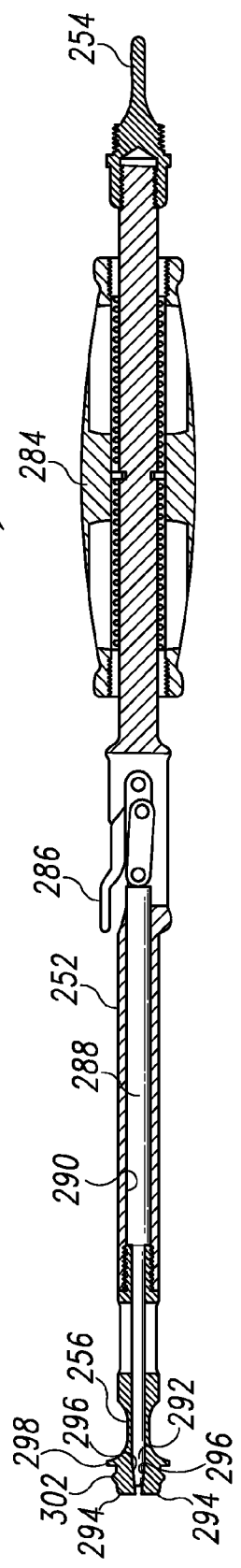

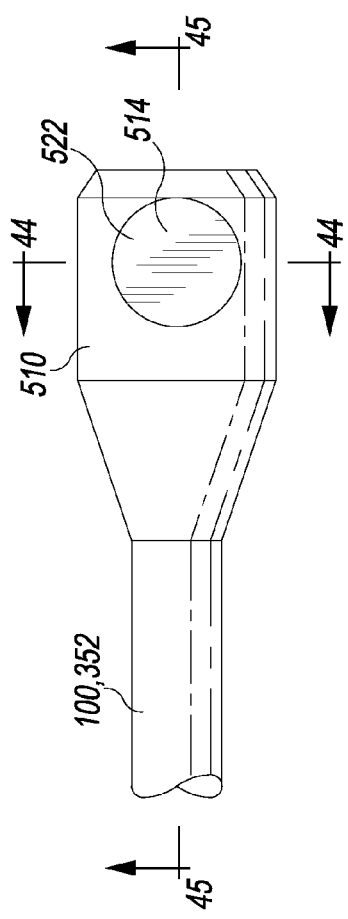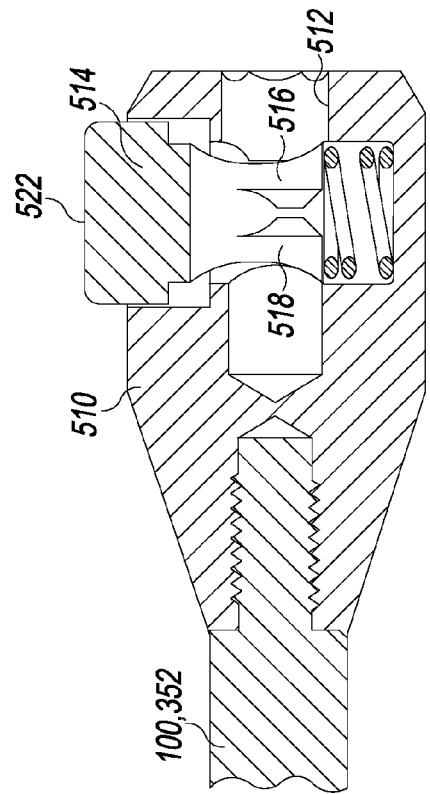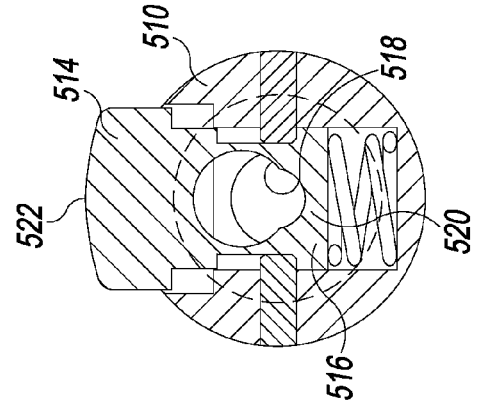

RECIPROCATING RASPS FOR USE IN AN ORTHOPAEDIC SURGICAL PROCEDURE

This application claims priority under 35 U.S.C. §119(e) to U.S. Provisional Patent Application Ser. No. 61/291,455 which was filed on Dec. 31, 2009, the entirety of which is hereby incorporated by reference.

CROSS REFERENCE

Cross reference is made to copending U.S. patent application Ser. No. 12/956,881 entitled "Reciprocating Rasps for Use in an Orthopaedic Surgical Procedure" which is assigned to the same assignee as the present application, filed concurrently herewith, and hereby incorporated by reference.

TECHNICAL FIELD

The present disclosure relates generally to an orthopaedic instrument for use in the performance of an orthopaedic joint replacement procedure, and more particularly to a reciprocating rasp for use in the performance of an orthopaedic joint replacement procedure.

BACKGROUND

During the lifetime of a patient, it may be necessary to perform a total shoulder replacement procedure on the patient as a result of, for example, disease or trauma. In a total shoulder replacement procedure, a humeral component having a prosthetic head is used to replace the natural head of the patient's humerus. The humeral component typically includes an elongated stem that is implanted into the intramedullary canal of the patient's humerus. In such a total shoulder replacement procedure, the natural glenoid surface of the scapula is resurfaced or otherwise replaced with a glenoid component that provides a bearing surface upon which the prosthetic head of the humeral component articulates.

As alluded to above, the need for a shoulder replacement procedure may be created by the presence of any one of a number of conditions. One such condition is the deterioration of the patient's scapula in the area proximate to the glenoid surface as a result of, for example, glenohumeral arthritis. In such a condition, the erosion of the patient's scapula is generally observed posteriorly on the glenoid surface. Such erosion of the scapula renders treatment difficult, if not impossible, with a conventional glenoid component. One way to treat such a condition is by the use of a modified glenoid component, known generally as an augmented glenoid component. An augmented glenoid component has a posterior edge that is thicker than the corresponding anterior edge.

From time-to-time, revision surgery is performed to replace a glenoid component. In such a revision surgery, the previously implanted glenoid component is surgically removed and a replacement glenoid component is implanted in the patient's glenoid. The subcondylar plate may be damaged or missing subsequent to revision surgery. Revision surgery may also result in defects, some of which may be fairly large, in the cancellous bone of the glenoid vault of the scapula. Fixation of a revision glenoid component can be difficult to achieve with the limited bone remaining on the glenoid vault of the scapula after the revision surgery has been performed. Vault-filling revision glenoid components have been developed that include a metal backing that extends into (i.e., "fills") the glenoid vault to replace the lost bone. A bearing component, generally made of polyethylene (e.g., UHMWPE) or other materials such as ceramics or metals, is then fixed to the implanted metal backing to create the bearing surface upon which the proximal end (e.g., a prosthetic head) of the humeral component articulates.

Simple surgical instruments such as revolving spherical or circular reamers are generally used to prepare the glenoid surface during a glenoid surgical procedure. This is sufficient since traditional glenoid components (i.e., non-augmented glenoid components or non-vault-filling glenoid components) typically have a uniform backside geometry that is either curved or flat, which makes glenoid preparation fairly straightforward. However, the use of glenoid components with complex backside geometries (e.g., augmented glenoid components or vault-filling glenoid components) makes bone preparation more of a challenge. A surgeon is forced to use a combination of reamers, saws, and burrs in the performance of a free-hand technique that requires frequent interruptions for intraoperative assessment to implant these complex components.

A similar condition can occur in the acetabulum of a patient's hip. Namely, deterioration of the patient's hip bone in the area proximate to the acetabulum can occur as a result of, for example, arthritis. Such erosion of the hip bone renders treatment difficult, if not impossible, with a conventional acetabular component. One way to treat such a condition is by the use of an acetabular augment component that replaces the diseased or damage bone tissue.

SUMMARY

According to one aspect, an augmented glenoid component includes a buttress on the posterior side of the component. The augmented glenoid component also includes an anchor peg with fins and a number of stabilizing pegs.

According to another aspect, a reciprocating rasp allows for the surgical preparation of the bone necessary for the implantation of an augmented glenoid component with such complex geometry. The use of the rasp allows the posterior glenoid to be prepared with a single instrument and in one precise and efficient step.

In an illustrative embodiment, the reciprocating rasp includes a shaft that has an end that fits into a reciprocating power tool. A cutting head located on the other end of the shaft has a geometry that matches that of the buttress of the augmented glenoid component. The cutting head of the rasp is covered in teeth. When the cutting head is advanced into the bone tissue of the glenoid with reciprocating motion, the teeth abrade the bone thereby gradually creating the shape required to accept the augmented glenoid component.

The reciprocating rasp also includes an alignment member for receiving a guide pin during an orthopaedic surgical procedure. In an illustrative embodiment, the alignment member is embodied as a pair of guide rings secured to the shaft of the rasp.

The rasp also includes a depth stop which bottoms out on the anterior surface of the glenoid when the cutting head has reached the desired depth.

According to another aspect, a vault component includes a number of inclined side walls which form a wedge-shaped body. The vault glenoid component includes a cavity and a number of screw holes for receiving bone screws to secure the component to the bone tissue of the patient's scapula.

According to another aspect, a reciprocating rasp allows for the surgical preparation of the bone necessary for the implantation of a vault glenoid component with such complex geometry. The use of the rasp allows the glenoid vault to be prepared with a single instrument and in one precise and efficient step.

In an illustrative embodiment, the reciprocating rasp includes a shaft that has an end that fits into a reciprocating power tool. A wedge-shaped cutting head located on the other end of the shaft has a geometry that matches that of the wedge-shaped vault glenoid component. The cutting head of the rasp is covered in teeth. When the cutting head is advanced into the bone tissue of the glenoid with the reciprocating motion, the teeth abrade the bone thereby gradually creating the wedge shape required to accept the vault glenoid component.

The reciprocating rasp also includes an alignment feature for receiving a guide pin during an orthopaedic surgical procedure. In an illustrative embodiment, the alignment member is embodied as an elongated alignment bore formed in the shaft of the rasp. A number of viewing widows are formed in the shaft of the rasp to permit visualization of the guide pin when it is positioned in the alignment bore.

According to another aspect, a acetabular augment component includes a curved outer surface which forms a half-hemispherically-shaped body. The acetabular augment component includes a cavity and a number of screw holes for receiving bone screws to secure the component to the bone tissue of the patient's hip bone.

According to another aspect, a reciprocating rasp allows for the surgical preparation of the bone necessary for the implantation of an acetabular augment component with such complex geometry. The use of the rasp allows the patient's acetabulum to be prepared precisely and efficiently.

In an illustrative embodiment, the reciprocating rasp includes a removable shaft that has an end that fits into a reciprocating power tool. Alternatively, the shaft may be used as a manual tool. A half-hemispherically-shaped cutting head may be coupled to the other end of the removable shaft. The cutting head has a geometry that matches that of the acetabular augment component. The cutting head of the rasp is covered in teeth. When the cutting head is advanced into the bone tissue of the acetabulum with the reciprocating motion, the teeth abrade the bone thereby gradually creating the complex shape required to accept the acetabular augment component.

The reciprocating rasp also includes an alignment feature for aligning the rasp to a trial instrument during an orthopaedic surgical procedure. In an illustrative embodiment, the alignment member is embodied as an elongated groove formed in the cutting head of the rasp which received an elongated tongue of the trial instrument.

BRIEF DESCRIPTION OF THE DRAWINGS

The detailed description particularly refers to the following figures, in which:

FIG. 25 is a side elevation view of a removable shaft that may be selectively coupled to the cutting head of the reciprocating rasp of FIGS. 21-23;

FIG. 26 is a cross sectional view of the removable shaft of FIG. 25;

FIG. 43 is a fragmentary side elevation view of another female connector that may be used as the chuck of a hand tool or power tool;

FIG. 44 is a cross sectional view of the female connector of FIG. 43 taken along the line 44-44 of FIG. 43, as viewed in the direction of the arrows;

FIG. 45 is a cross sectional view of the female connector of FIG. 43 taken along the line 45-45 of FIG. 43, as viewed in the direction of the arrows;

DETAILED DESCRIPTION OF THE DRAWINGS

Figure 1:
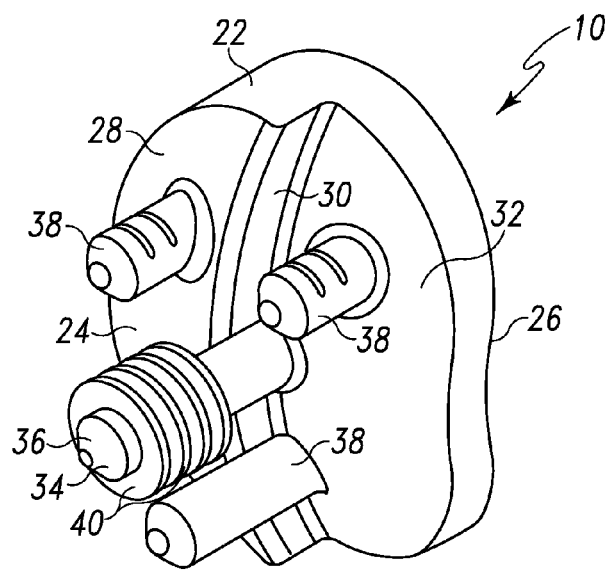
FIG. 1 is a perspective view of an augmented glenoid component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figures 2, 3:
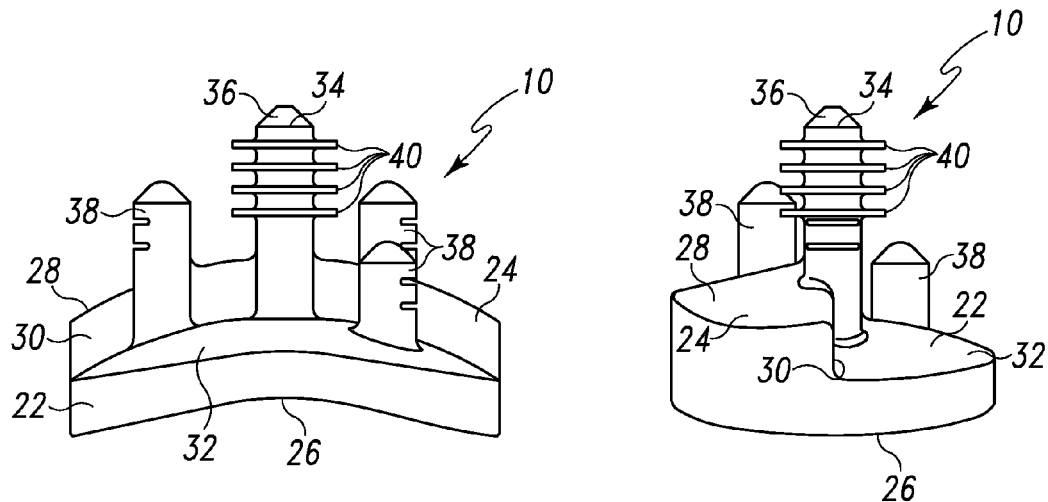
FIGS. 2 and 3 are side elevation views of the augmented glenoid component of FIG. 1.

Referring now to FIGS. 1-3, there is shown an augmented glenoid component 10. The augmented glenoid component 10 includes a body 22 having a concave surface 26 on one end thereof. The concave surface 26 of the body 22 provides a smooth bearing surface upon which a natural or prosthetic humeral head articulates. A buttress 24 extends away from the anterior medial surface 32 of the body 22 opposite the concave surface 26. The posterior medial surface 28 of the buttress 24 is substantially flat in the anterior/posterior direction and rounded (i.e., convex) in the superior/inferior direction. The anterior medial surface 32 is rounded (i.e., convex) in all directions, but may include flat portions to fit the need of a given design. A side surface 30 extends perpendicularly from the posterior medial surface 28 to the anterior medial surface 32. Alternatively, the side surface 30 may be angled relative to both surfaces 28, 32.

The augmented glenoid component 10 also includes an anchor peg 34. The anchor peg 34 extends perpendicularly from the anterior medial surface 32. The anchor peg 34 includes a tapered head 36 that functions as a lead-in to facilitate insertion into a hole drilled or otherwise formed in the glenoid surface of the patient's scapula. The glenoid component 10 also includes a plurality of stabilizing pegs 38. One of the pegs 38 extends from the anterior medial surface 32, with another of the pegs 38 extending from the posterior medial surface 28 of the buttress 24. Another of the three stabilizing pegs 38 extends from both the anterior medial surface 32 and the buttress 24—i.e., it straddles the buttress 24 and the anterior medial surface 32. Generally, the stabilizing pegs 38 are shorter than the anchor peg 34. Moreover, some of the stabilizing pegs 38 (e.g., the one extending from the anterior medial surface 32) are shorter than the others, although other configurations may be used. The stabilizing pegs 38 are received into a number of corresponding holes drilled or otherwise formed in the glenoid surface of the patient's scapula.

In the illustrative embodiment described herein, the augmented glenoid component 10 is embodied as a monolithic molded component. That is, the body 22, the anchor peg 34, and the stabilizing pegs 38 are integrally molded using a polymer such as polyethylene. One example of a suitable polyethylene is ultrahigh molecular weight polyethylene (UHMWPE). In addition to polymers, the augmented glenoid component 10 may be made from ceramic, metal, or a composite material. Examples of these materials include alumina, zirconia, and alumina/zirconia composite or composite material.

The anchor peg 34 includes a plurality of radial fins 40. The fins 40 are deformable. This allows the anchor peg 34 to fit into an anchor bore drilled in the glenoid surface of the patient's scapula, but resist removal or "pull out" of the anchor peg 34. Any number or size of radial fins 40 may be included on the anchor peg 34. In addition, although each of the fins 40 is herein described with the same sized outer diameter, it should be appreciated that other configurations are also contemplated for use. For example, the fins 40 may be provided in a tapered configuration in which the respective outer diameters of the fins 40 gradually increases from the distal end of the anchor peg 34 to the proximal end of the anchor peg 34 (i.e. the ring positioned on the distal end of the anchor peg 34 has a smaller diameter relative to the ring positioned near the proximal end of the anchor peg 34).

The fins 40 are configured to slightly deform when the anchor peg 34 is inserted into an anchor hole drilled in the patient's glenoid. This is caused when the fins 40 are advanced into the anchor hole since it is drilled to have a diameter which is slightly larger than the diameter of a shaft of the anchor peg 34, yet smaller than the outer diameter of the fins 40 thereby causing deformation of the fins 40 upon contact with the sidewalls of the drilled hole as the fins 40 are "forced" into the hole. Such deformation of the fins 40 secures the augmented glenoid component to the scapula by providing resistance to pull out of the anchor peg 34 from the drilled anchor hole much in the same way that the threads of a screw provide resistance to pull out of the screw from the material into which it is driven. In addition, over a period of time subsequent to implantation of the augmented glenoid component 10 to the patient's scapula, bone tissue or other types of tissue will grow into the spaces between the fins 40 thereby providing further resistance to pull out of the anchor peg 34 from the drilled hole.

The stabilizing pegs 38 prevent rotation or other types of movement of the augmented glenoid component 10 relative to the scapula once the glenoid component 10 has been implanted. The distal end of each of the stabilizing pegs 38 has a conical tip which functions as a "lead in" to facilitate insertion of the stabilizing pegs 38 into respective stabilizing holes drilled in the glenoid surface of the patient's scapula.

The stabilizing pegs 38 may be arranged in any orientation on the body 22 that fits the needs of a given design of an augmented glenoid component. In addition, it should be appreciated that any number of stabilizing pegs 38 may be utilized to fit the needs of a given design of an augmented glenoid component. Examples of such variations are shown in commonly-owned U.S. Pat. No. 6,699,289, the entirety of which is hereby incorporated by reference.

Figures 4, 5:
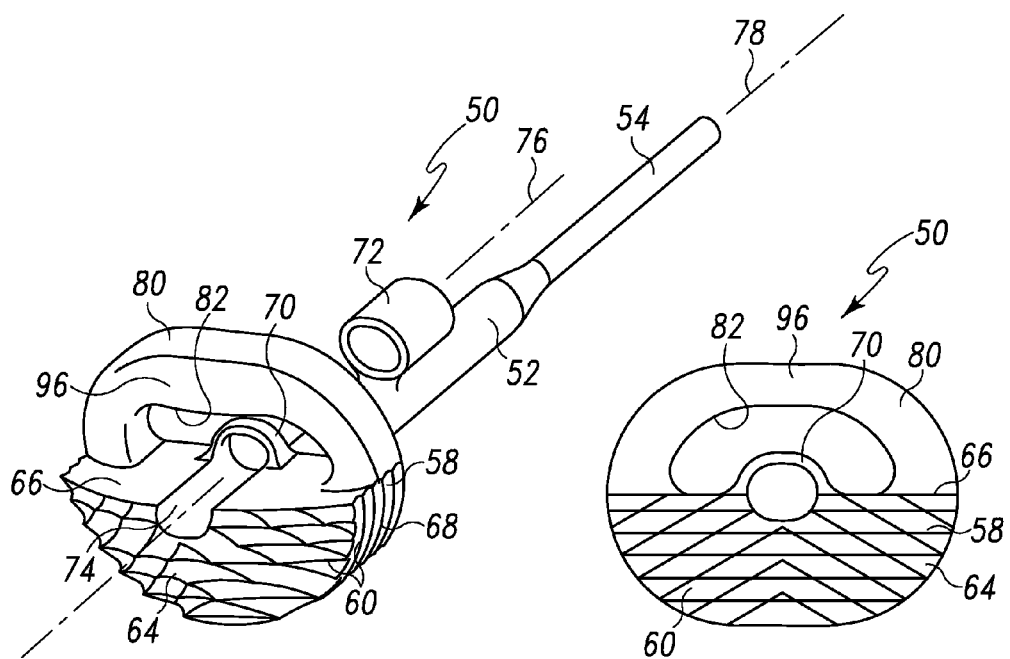
FIG. 4 is a perspective view of a reciprocating rasp for use in an orthopaedic surgical procedure to implant the augmented glenoid component of FIG. 1.
FIG. 5 is an elevation view of the cutting head of the reciprocating rasp of FIG. 4.
Figure 6:
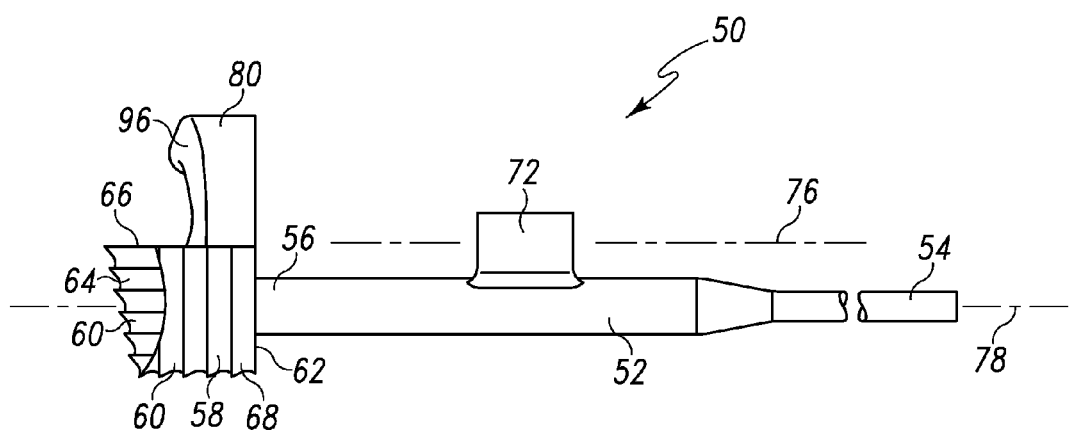
FIG. 6 is a side elevation view of the reciprocating rasp of FIG. 4.

Referring now to FIGS. 4-6, there is shown a reciprocating rasp 50 that may be used for the surgical preparation of the patient's glenoid to facilitate implantation of the complex geometry associated with the augmented glenoid component 10. The rasp 50 includes a tapered shaft 52 having a proximal end 54 that fits into the chuck of a reciprocating power tool 100 (see FIGS. 7 and 8). The reciprocating rasp 50 also includes a cutting head 58 secured to the opposite, distal end 56 of the shaft 52. As will be discussed in greater detail below, the geometry of the cutting head 58 corresponds with the geometry of the buttress 24 of the augmented glenoid component 10. The cutting head 58 of the reciprocating rasp 50 includes a plurality of cutting teeth 60. When the rasp 50 is advanced into engagement with the glenoid surface of the patient's scapula with reciprocating motion, the cutting teeth 60 of the reciprocating rasp 50 abrade or otherwise cut the bone tissue of the scapula thereby gradually creating notch possessing the geometry (i.e., the shape) required to accept the buttress 24 of the augmented glenoid component 10.

The cutting head 58 includes a generally D-shaped (i.e., half-elliptical shaped) lateral or backside surface 62. Opposite the lateral surface 62 is a lead cutting surface 64. The lead cutting surface 64 of the cutting head 58 mimics the shape of the posterior medial surface 28 of the buttress 24 of the augmented glenoid component 10. That is, the lead cutting surface 64 is substantially flat in the anterior/posterior direction and rounded (i.e., convex) in the superior/inferior direction. The lead cutting surface 64 is defined by the outer surfaces of a plurality of the cutting teeth 60. A substantially flat, smooth anterior sidewall 66 extends upwardly from the lateral surface 62 of the cutting head 58 to the lead cutting surface 64. As shown in FIG. 4, the anterior sidewall 66 is devoid of cutting teeth. A curved sidewall 68 extends upwardly from the lateral surface 62 of the cutting head 58 to the lead cutting surface 64. The curved posterior sidewall 68 extends from one end of the anterior sidewall 66 to the other and defines the curved posterior portion of the cutting head's generally D-shaped design. Like the lead cutting surface 64, the posterior sidewall 68 is defined by the outer surfaces of a plurality of the cutting teeth 60.

The reciprocating rasp 50 also includes an alignment member that, as will be discussed below in greater detail, aligns the rasp 50 to a guide pin. The alignment member may be embodied any of numerous different structures which are configured to coordinate with a surgically-implanted guide pin to position the cutting head 58 of the rasp 50 in a desired location relative to the guide pin. Examples of structures that may function as the alignment member include one or more sleeves, rings, cannulated bosses, cylinders, guides, hooks, or any other similar structure capable of receiving a guide pin.

In the illustrative embodiment described herein, the alignment member is embodied as a pair of rings 70, 72. As can be seen in FIG. 4, the ring 70 is located proximate to the anterior sidewall 66 of the rasp's cutting head 58. In the illustrative embodiment described herein, the ring 70 is formed in the anterior sidewall 66, although it may be embodied as a separate component welded or otherwise secured to the rasp 50. The anterior sidewall 66 also includes a curved channel 74 formed therein. The curved channel 74 provides clearance for the guide pin as it enters the ring 70.

The ring 72 is located on the rasp's tapered shaft 52 at a location between its proximal end 54 and its distal end 56. Like the ring 70, the ring 72 may be integrally formed with the rasp's tapered shaft 52 or may be embodied as a separate component welded or otherwise secured to the shaft 52. Each of the rings 70, 72 is sized and shaped to allow for the free, reciprocating motion of the rasp 50, while retaining the rasp 50 on the guide pin to maintain the desired orientation of the rasp 50. As shown in FIG. 4, the center points of the rings 70, 72 lie along a single line 76 that is parallel to, and spaced apart from, the longitudinal axis 78 of the rasp's tapered shaft 52. As such, the guide axis 76 is offset from the shaft axis 78. The size of the offset may vary and is related not only to the size/shape of the rasp, but also in part, to the surgical instrumentation and method for placement of the guiding pin.

The reciprocating rasp 50 also includes a depth stop 80 secured to the rasp's cutting head 58. As will be described below in greater detail, the depth stop 80 bottoms out on the reamed anterior surface of the patient's glenoid to ensure the posterior glenoid surface is prepared to the desired depth relative to the anterior glenoid surface. In other words, the depth stop 80 creates a spatial relationship (i.e., a depth) between the surgically-prepared anterior and posterior glenoid surfaces which matches the distance between the posterior medial surface 28 of the glenoid component's buttress 24 and its anterior medial surface 32. Such a distance is defined by the height of the side surface 30 that extends perpendicularly from the posterior medial surface 28 of the buttress to the anterior medial surface 32 of the augmented glenoid component 10.

Like the alignment member described above, the depth stop 80 may be embodied as a number of different structures. For example, the depth stop 80 may be embodied as one or more tabs, bars, flanges, other similar structures configured to bottom out on the anterior surface of the patient's glenoid to prevent further penetration of the cutting head 58 into the posterior surface of the patient's glenoid. In the exemplary embodiment described herein, the depth stop 80 is embodied as a generally D-shaped bar that has its ends secured to the anterior sidewall 66 of the rasp's cutting head 58. Such a configuration creates a window 82 through which the surgeon can visualize the patient's glenoid surface without the surgeon's line of sight being obstructed by the depth stop 80.

Figure 7:
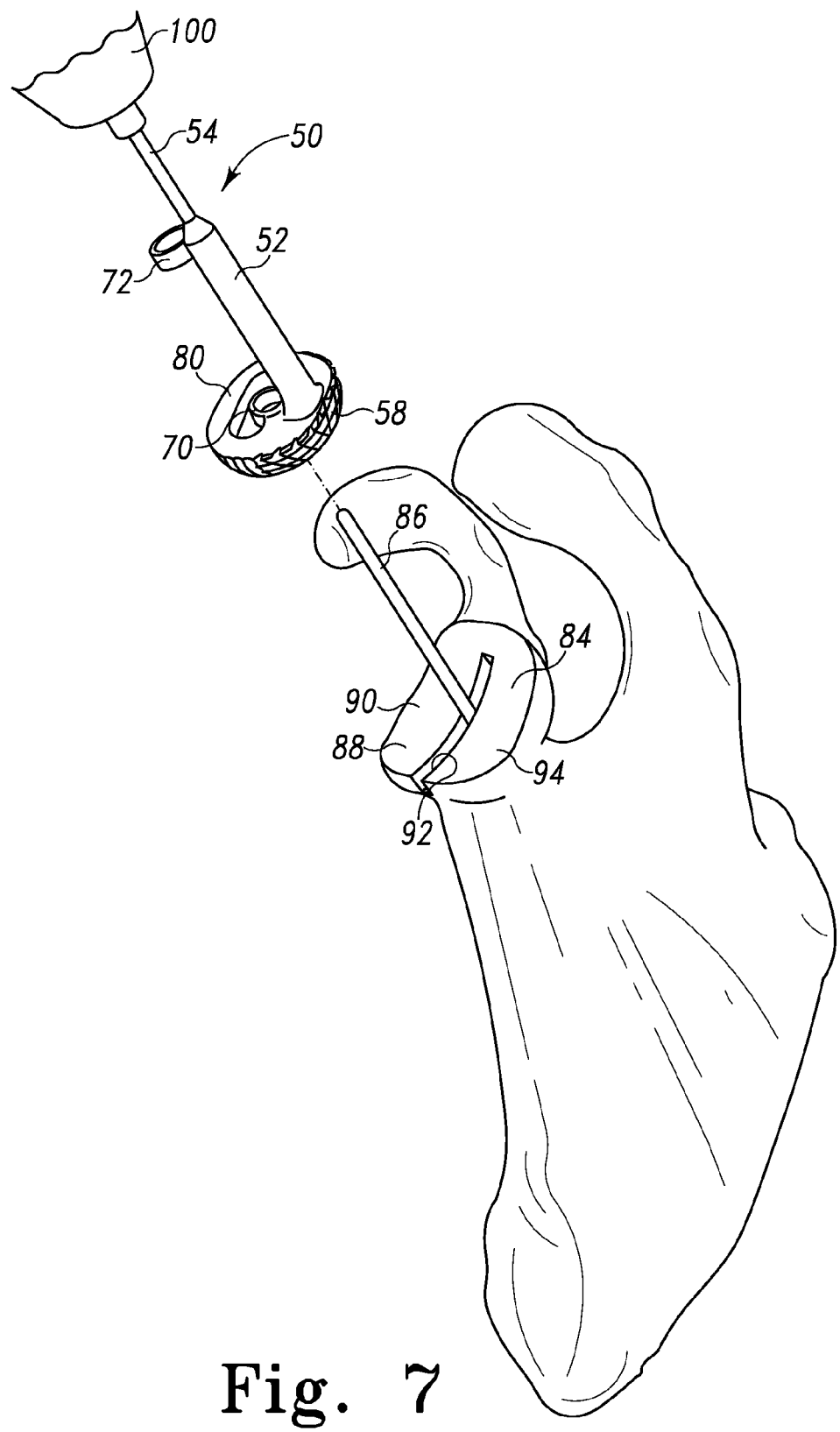
FIG. 7 is a perspective view showing a guide pin inserted in the glenoid of a patient during an orthopaedic surgical procedure to implant the augmented glenoid component of FIG. 1.
Figure 8:
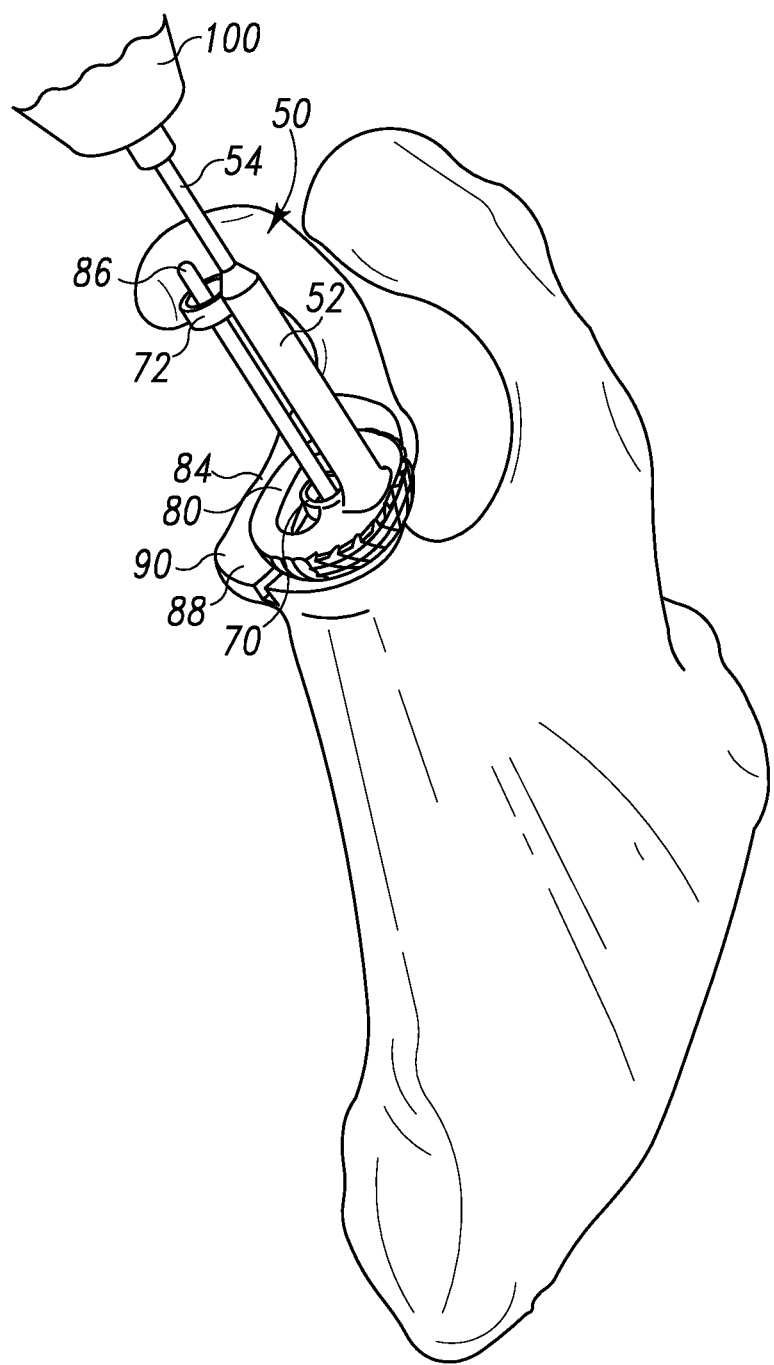
FIG. 8 is a view similar to FIG. 7 showing the reciprocating rasp of FIGS. 4-6 during rasping the patient's glenoid.
Figure 9:
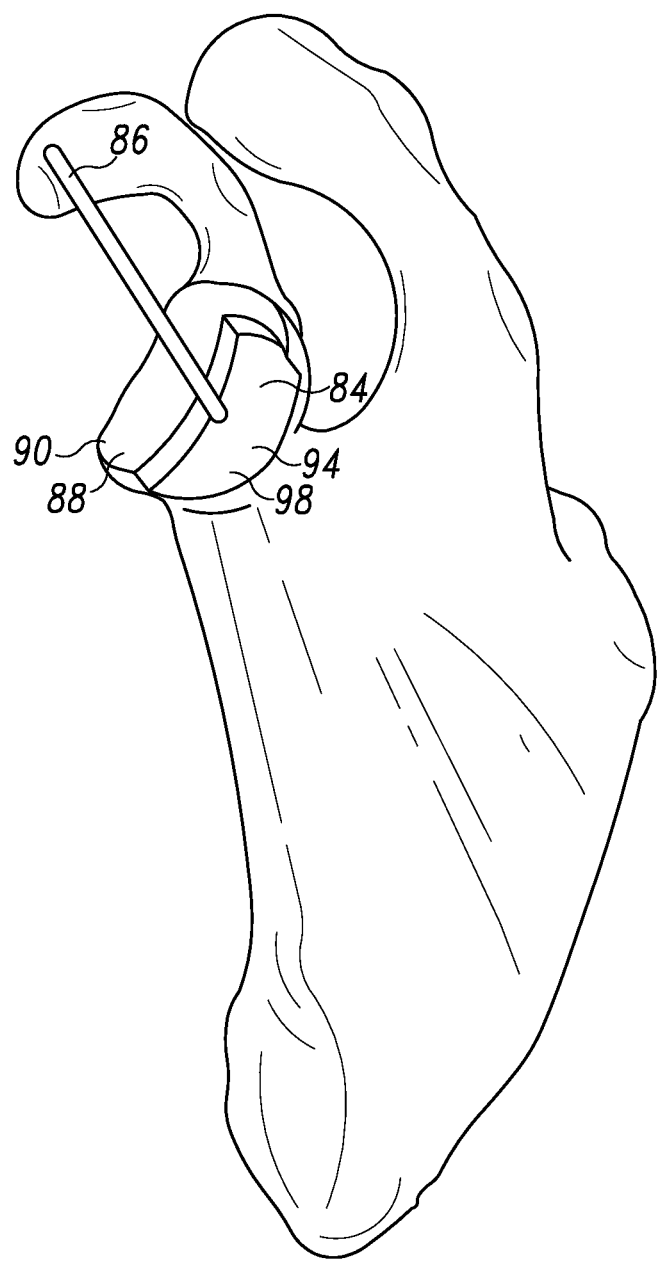
FIG. 9 is a view similar to FIG. 8 showing the patient's glenoid after it has been rasped with the reciprocating rasp of FIGS. 4-6.

Referring now to FIGS. 7-9, there is shown a surgical procedure in which the reciprocating rasp 50 is used to surgically prepare the patient's glenoid 84 for implantation of the augmented glenoid component 10. The surgical procedure begins with preoperative planning in which, amongst other things, a thin cut (1 mm) axial CT scan with the gantry positioned perpendicular to the plane of the glenoid and plane of the scapula is obtained. A single axial slice just below the mid-equator of the glenoid is obtained for measurement of glenoid version. Correction of retroversion may then be individualized to the patient. With the preoperative planning complete, the patient's soft tissue is dissected and retracted in order to allow access to the glenoid. Full (i.e., 360°) exposure of the bony glenoid is typically achieved.

As shown in FIG. 7, a guide pin 86 is then inserted in the center of the glenoid 84 in an orientation that will allow for the desired amount of retroversion correction. This can be accomplished using one of a number of different pin placement devices. The guide pin 86 may be scored in locations along its length to allow for controlled breakage to adjust the length of the pin 86 subsequent to being inserted. Specifically, at any point in the procedure, the guide pin 86 can be shortened to a more desirable length by placing a handle just above a score mark and a needle driver just below the same score mark and bending the pin 86 at the score mark. In the illustrative procedure described herein, two to three inches of the pin 86 protrude laterally from the glenoid.

A sizer pin guide (not shown) may then be placed over the guide pin 86. The sizer pin guide is used determine the optimal size augmented glenoid component for the patient's glenoid. Typically, a desired size of an augmented glenoid component covers as much of the glenoid surface as possible without overhanging the periphery of the bone surface.

The anterior surface 88 of the patient's glenoid 84 is then reamed in a typical manner. In particular, a spherical reamer (not shown) is used over the guide pin 86 to ream the anterior surface 88 of the glenoid and create an even, concave surface from the superior edge of the glenoid 84 (i.e., 12 o'clock) to the inferior edge of the glenoid 84 (i.e., 6 o'clock). This reamed surface 90 is the final surgically-prepared surface that contacts the anterior medial surface 32 of the augmented glenoid component 10 when it is implanted. It should be appreciated that if the spherical reamer used is smaller than the superior/inferior dimension of the augmented glenoid component 10, a small amount of bone on the superior and/or inferior aspects of the anterior glenoid will remain. This remaining bone may be removed with a peripheral reamer (not shown). A hand burr (not shown) may be alternatively used to remove the remaining bone. The reamed surface 90 of the patient's anterior glenoid 84 is shown in FIG. 7.

A depth gauge (not shown) may then be placed over the guide pin 86. The contact and conformity between the back surface of the depth gauge and the prepared anterior glenoid surface 90 is the determined. Further preparation of the bone may then be performed if the contact and conformity is not to the surgeon's satisfaction. The maximum depth of the posterior glenoid defect is measured by inserting a depth probe (not shown) through the depth gauge. In one illustrative instrument, three holes in the posterior half of the depth gauge are provided so that three different locations and their respective depths can be evaluated. In most cases the greatest depth of the defect is on the posterior, inferior quadrant of the glenoid. Such an evaluation allows for implant selection (i.e., selection of a particularly sized augmented glenoid component 10). For example, if the maximum depth is 3 mm or less, an augmented glenoid component 10 with a 3 mm augment (i.e., a 3 mm thick buttress 24) is needed. If the depth measured is between 3 mm and 5 mm, an augmented glenoid component 10 with a 5 mm augment is needed. If the depth measured is between 5 mm and 7 mm, an augmented glenoid component 10 with a 7 mm augment is needed. In the illustrative procedure described herein, if the depth measured is more than 7 mm, additional bone may need to be removed from the anterior surface 88 of the patient's glenoid 84. In this illustrative case, the amount of additional bone to be removed is equal to the maximum defect minus 7 mm.

The appropriate size posterior preparation guide (not shown) is then placed over the guide pin 86 so that it firmly and concentrically contacts the prepared anterior glenoid surface 90. The posterior window in the guide defines the boundaries of the posterior surface 94 of the glenoid 84 to be prepared to accept the buttress 24 of the augmented glenoid component 10, and it can be used as a template for marking these boundaries with either a sterile pen or a bovie.

Once the boundaries of the buttress 24 have been marked, the posterior glenoid is surgically prepared. At the outset, a saw blade or other surgical tool may be used to create a channel 92 in the midline of the patient's glenoid 84 in the superior/inferior direction. The channel 92 is created parallel to the cutting surface of the guide. The depth of the channel 92 is guided by the etch marks on the saw blade. For example, for a 3 mm augment, the saw blade should be advanced until the 3 mm etch mark is at the same level as the lateral surface of the posterior preparation guide. This creates a wall of bone in the center of the glenoid 84 that serves as the perpendicular step between the anterior and posterior halves of the medial surface of the augmented glenoid component 10—i.e., a surgically prepared surface that corresponds with the side surface 30 of the augmented glenoid component 10. The channel 92 is shown in FIG. 7. A hand burr (not shown) may then be used to remove any hard, subchondral bone on the posterior surface 94 of the glenoid 84.

A reciprocating rasp 50 sized to match the buttress 24 of the selected augmented glenoid component 10 is then obtained from a number of differently-sized rasps 50 and used to complete the posterior preparation. The proximal end 54 of the tapered shaft 52 of the selected reciprocating rasp 50 is then secured within the chuck of the reciprocating power tool 100. Once chucked, the rasp is advanced over the guide pin 86. In particular, the guide pin 86 is first advanced through the guide ring 70 located proximate to the rasp's cutting head 58 and thereafter the guide ring 72 located proximate to the mid-portion of the rasp's tapered shaft 52. Advancing the guide pin 86 through the rings 70, 72 aligns the rasp's cutting head 58 with the marked boundaries of the posterior surface 94 of the glenoid 84 (i.e., the portion of the posterior surface 94 of the glenoid 84 that is to be surgically prepared to accept the buttress 24 of the augmented glenoid component 10). Centering the guide pin 86 within the rings 70, 72 also controls (i.e., guides) the trajectory of the reciprocating rasp 50.

As shown in FIG. 8, once the reciprocating rasp 50 is inserted over the guide pin 86, the surgeon activates the reciprocating power tool 100 and advances the lead cutting surface 64 of the cutting head 58 into contact with posterior surface 94 of the glenoid 84. As the rasp 50 is advanced inwardly toward the patient's glenoid 84, the reciprocating motion of the rasp 50 abrades the bone and continues to remove bone until the leading surface 96 of the depth stop 80 (see FIGS. 4-6) bottoms out on the reamed anterior surface 90 of the patient's glenoid 84. This ensures the rasped posterior glenoid surface 98 is prepared to the desired depth relative to the reamed anterior glenoid surface 90. When the depth stop 80 of the rasp 50 contacts the reamed anterior surface 90 of the glenoid 84 in such a manner, the posterior preparation of the glenoid 84 is complete—i.e., the rasped posterior glenoid surface 98 has been completed. The reciprocating rasp 50 is then removed from the guide pin 86.

It should be appreciated that in lieu of completing the rasped posterior glenoid surface 98 with a single rasp 50, a number of differently-sized rasps 50 may be used. In particular, a number of progressively larger-sized rasps 50 may be used to produce the desired final size. For example, initial rasping may be performed with a rasp 50 having a relatively small cutting head 58. Thereafter, one or more additional rasps 50 having progressively larger cutting heads 58 may be used to perform subsequent rasping to form a larger cavity of the desired final size.

A bone preparation assessor (not shown), which is sized to mimic the medial surfaces of the selected augmented glenoid component 10, is placed over the guide pin 86 and used to determine whether the anterior reaming and posterior rasping of the bony surfaces was sufficient to accommodate the selected augmented glenoid component 10. The bone preparation assessor generally makes full and concentric contact with the prepared glenoid surfaces. If high spots on the bone are preventing the bone preparation assessor from seating completely, an impactor, tamp, or other instrument may be inserted over the guide pin 86 and used to make the prepared glenoid surfaces more conforming. The fit of the bone preparation assessor may then be assessed again.

A cannulated center drill (not shown) of the appropriate length based on the step height of the buttress 24 of the selected augmented glenoid component 10 is inserted over the guide pin 86. The drill is then used to prepare (i.e., drill) the glenoid 84 to accept the anchor peg 34 of the augmented glenoid component 10. The drill is advanced until it bottoms out on the reamed anterior surface 90 of the glenoid 84. Once the center hole for the anchor peg 34 has been drilled, a pin puller or other instrument (not shown) is used to grasp and remove the guide pin 86.

A peripheral drill guide (not shown) specific to the selected augmented glenoid component 10 is inserted into the drilled center hole. The holes for the stabilizing pegs 38 are then drilled with the assistance of the drill guide.

An implant trial (not shown) is placed into the prepared glenoid, and its fit is assessed. Full and concentric contact between the medial side of the trial and the prepared surfaces of the bone is generally desired. If this is not the case, some or all of the prior bone preparation steps may be repeated. If the fit is adequate, the trial is removed.

Finely morselized bone retrieved during the glenoid preparation is used to create a "bone paste." This bone paste is interposed between the fins 40 of the anchor peg 34 of the augmented glenoid component 10 to facilitate tissue integration. Bone cement, such as PMMA-based bone cement, is placed in the peripheral holes (i.e., the holes for the stabilizing pegs 38) of the prepared glenoid 84 and pressurized using a fingertip. The augmented glenoid component 10 is then inserted, and a glenoid impactor (not shown) is used to seat the component 10 until there is complete contact with the perimeter of the glenoid 84. Pressure on the implanted component 10 is maintained until the cement has hardened.

Figure 10:
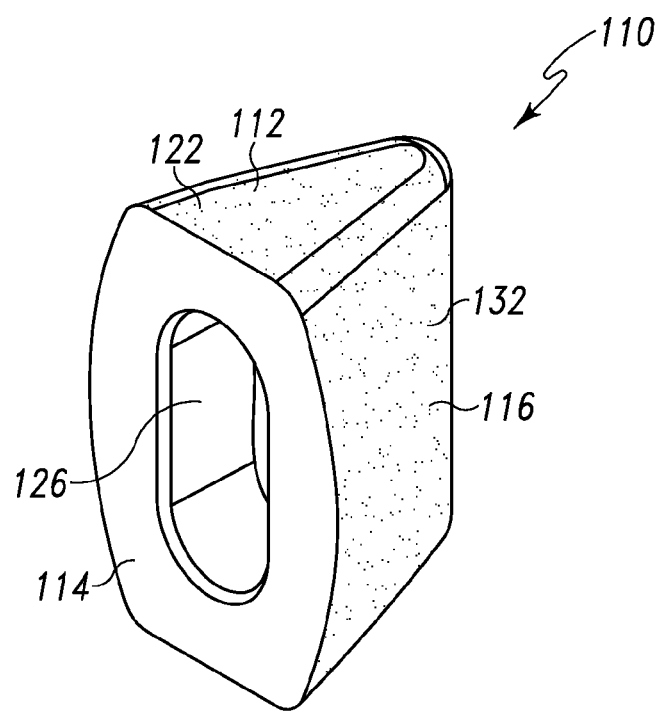
FIG. 10 is a perspective view of a vault glenoid component.
Figure 11:
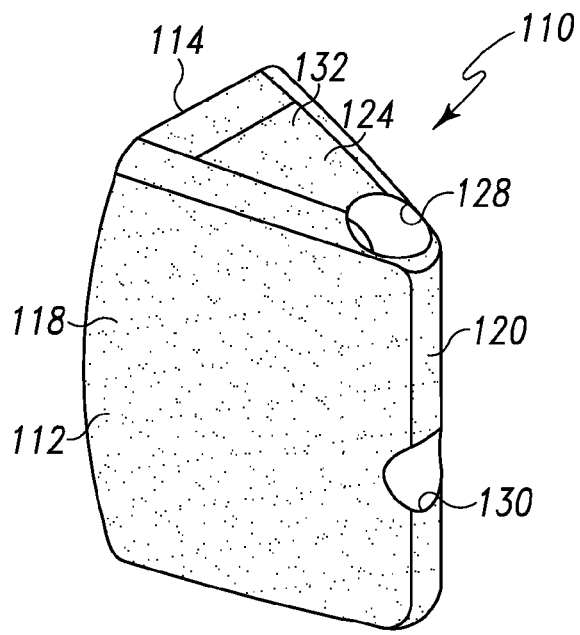
FIG. 11 is a perspective view of the other side of the vault glenoid component of FIG. 10.

Referring now to FIGS. 10 and 11, there is shown a vault-filling (or simply, "vault") glenoid component 110. The vault glenoid component 110 includes a generally wedge-shaped metal body 112 having a substantially planar lateral surface 114. The body 112 has an anterior surface 116 and a posterior surface 118 that extend medially away from the lateral surface 114. The anterior surface 116 and the posterior surface 118 mate at a rounded medial surface 120. A superior surface 122 and an inferior surface 124 also extend medially away from the lateral surface 114 and mate at the rounded or pointed medial surface 120.

The body 112 of the vault glenoid component 110 has a cavity 126 formed therein. As will be discussed below in more detail, either a concave polymer bearing or a convex metal or ceramic head may be secured to the vault glenoid component 110 once it is implanted in a patient's glenoid. Both of such components (i.e., the bearing and the metal head) include a locking feature that is positioned and locked in the cavity 126.

As can be seen in FIG. 11, an angled screw hole 128 is formed in the inferior surface 124 of the vault glenoid component 110. The screw hole 128 opens into the cavity 126. Another screw hole 130 is formed in the rounded medial surface 120 and likewise opens into the cavity 126. As will be discussed below in greater detail, the tips of bone screws are inserted through the cavity 126, into the screw holes 128, 130, and thereafter driven into bone tissue to secure the vault glenoid component 110 to the patient's scapula.

The vault glenoid component 110 is made of an implant grade metal such as stainless steel, cobalt chrome, or titanium, although other metals or alloys may be used. Moreover, the bone contacting surfaces of the vault glenoid component have a porous material 132 disposed thereon. Specifically, the anterior surface 116, posterior surface 118, medial surface 120, superior surface 122, and inferior surface 124 are coated with the porous material 132, with the lateral surface 114 being devoid of such porous material. The porous material 132 is of the type commonly used in various orthopaedic components to enhance bone tissue ingrowth into the component.

Figure 12:
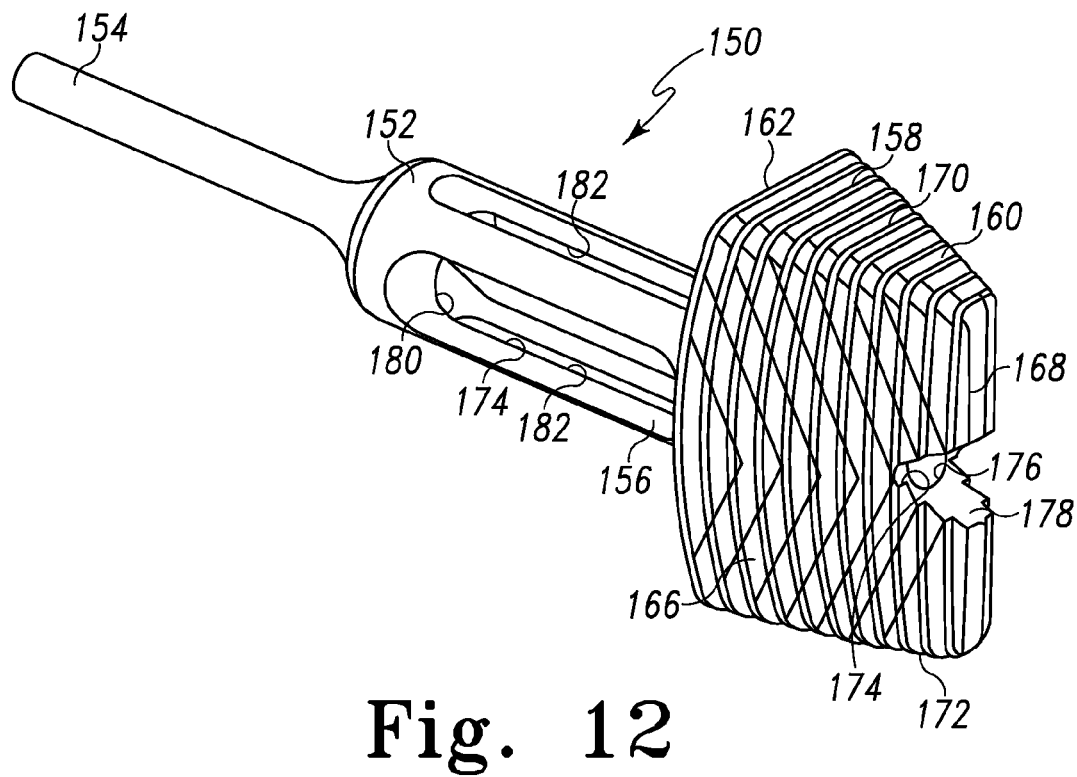
FIG. 12 is a perspective view of a reciprocating rasp for use in an orthopaedic surgical procedure to implant the vault glenoid component of FIG. 10.
Figure 13:
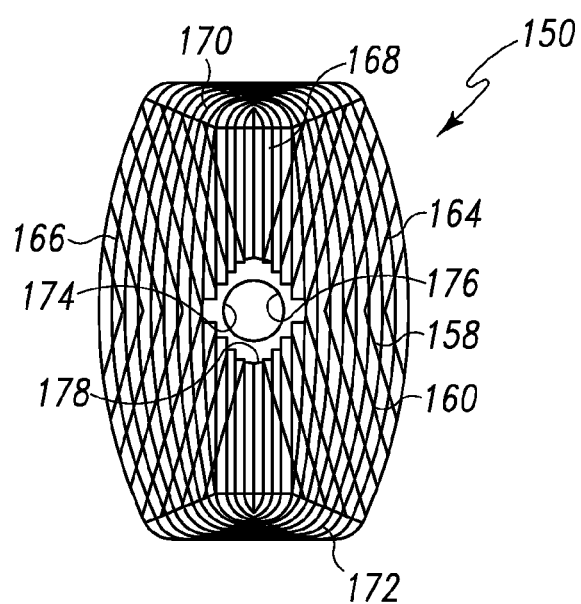
FIG. 13 is an elevation view of the cutting head of the reciprocating rasp of FIG. 12.
Figure 14:
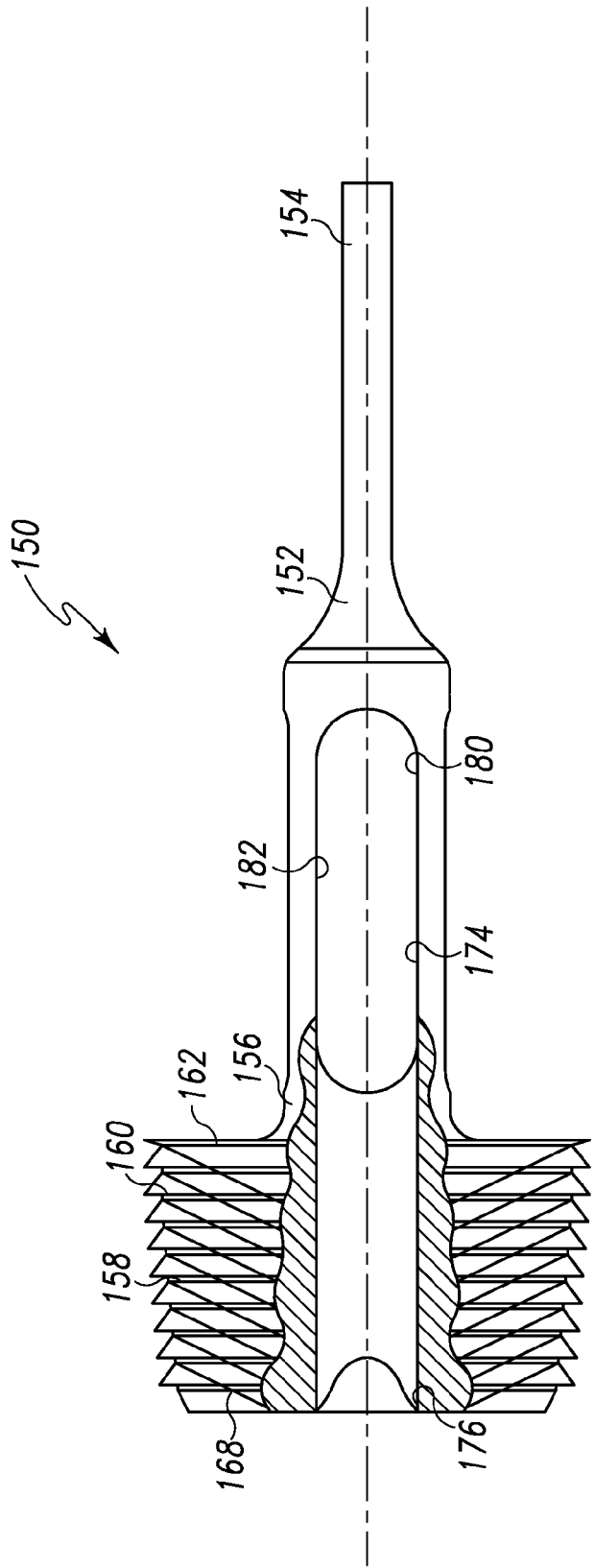
FIG. 14 is a side elevation view of the reciprocating rasp of FIG. 12 with a portion thereof cutaway to show the rasp's alignment bore.

Referring now to FIGS. 12-14, there is shown a reciprocating rasp 150 that may be used for the surgical preparation of the patient's glenoid to facilitate implantation of the complex geometry associated with the vault glenoid component 110. The rasp 150 includes a tapered shaft 152 having a proximal end 154 that, like the rasp 50 described above, fits into the chuck of the reciprocating power tool 100 (see FIGS. 15 and 16). The reciprocating rasp 150 also includes a wedge-shaped cutting head 158 secured to the opposite, distal end 156 of the shaft 152. As will be discussed in greater detail below, the geometry of the cutting head 158 corresponds with the wedge-shaped geometry of the vault glenoid component 110. The cutting head 158 of the reciprocating rasp 150 includes a plurality of cutting teeth 160 that are similar in geometry to the cutting teeth 60 of the reciprocating rasp 50 described above. When the rasp 150 is advanced into engagement with the glenoid vault of the patient's scapula with reciprocating motion, the cutting teeth 160 of the reciprocating rasp 150 abrade or otherwise cut the bone tissue of the scapula thereby gradually creating a cavity possessing the geometry (i.e., the shape) required to accept wedge-shaped vault glenoid component 110.

The cutting head 158 includes a lateral surface 162 which closely mimics the size and shape of the lateral surface 114 of the vault glenoid component 110. The cutting head 158 also includes an anterior cutting surface 164 which mimics the size and shape of the anterior surface 116 of the vault glenoid component 110, and a posterior cutting surface 166 which mimics the size and shape of the posterior surface 118 of the vault glenoid component 110. The cutting surfaces 164, 166 extend away from the cutting head's lateral surface 162 and mate at a rounded lead cutting surface 168 that mimics the size and shape of the rounded medial surface 120 of the vault glenoid component 110. A superior cutting surface 170 and an inferior cutting surface 172 also extend medially away from the cutting head's lateral surface 162 and mate at the lead cutting surface 168. The superior cutting surface 170 and the inferior cutting surface 172 mimic the size and shape of the superior surface 122 and the inferior surface 124 of the vault glenoid component 110, respectively. The cutting surfaces 164, 166, 168, 170, and 172 are defined by the outer surfaces of their cutting teeth 160.

Like the reciprocating rasp 50 described above in regard to FIGS. 1-9, the reciprocating rasp 150 also includes an alignment member or feature that, as will be discussed below in greater detail, aligns the rasp 150 to a guide pin 186 during a surgical procedure. The alignment member or feature may be embodied as any of numerous different structures or openings which are configured to coordinate with a surgically-inserted guide pin 186 to position the cutting head 158 of the rasp 150 in a desired location relative to the guide pin 186. Examples of structures that may function as the alignment member include one or more sleeves, rings, cannulated bosses, cylinders, guides, hooks, or any other similar structure capable of receiving a guide pin.

In the illustrative embodiment described herein, the alignment member or feature is embodied as an elongated bore 174 that extends through the cutting head 158 and into the shaft 152 (see FIG. 14). As can be seen in FIGS. 13 and 14, one end 176 of the alignment bore 174 is defined in (i.e., opens through) the lead cutting surface 168 of the cutting head 158. Specifically, the lead cutting surface 168 of the cutting head 158 has a generally V-shaped notch 178 formed therein. The end 176 of the alignment bore 174 opens into the notch 178. The notch 178 provides clearance for the guide pin and functions as a lead-in for the guide pin during pin insertion.

The opposite end 180 of the alignment bore 174 is located in the rasp's tapered shaft 152 at a location between its proximal end 154 and its distal end 156. The end 180 is located approximately in the middle of the shaft 152 near where the shaft tapers down to its smaller diameter proximal end 154. As shown in FIG. 14, the center line of the alignment bore 174 and the longitudinal axis of the reciprocating rasp 150 lie on the same line.

The portion of the tapered shaft 152 containing the alignment bore 174 has a number of slotted openings or "viewing windows" 182 defined therein. The viewing windows 182 allow the surgeon to visualize the guide pin as it is received in the alignment bore 174. In doing so, the surgeon can ensure that the guide pin does not bottom out against the curved sidewall that forms the interior end 180 of the alignment bore 174.

Similarly to the reciprocating rasp 50 described above, the vault reciprocating rasp 150 may be embodied with a depth stop (not shown). In a similar manner to as described above, such a depth stop bottoms out on the surface of the patient's glenoid to ensure the patient's glenoid surface is prepared to the desired depth. The depth stop of the vault reciprocating rasp 150 may be embodied as a number of different structures. For example, the depth stop may be embodied as one or more tabs, bars, flanges, other similar structures configured to bottom out on the surface of the patient's glenoid to prevent further penetration of the cutting head 158. In an exemplary embodiment, the depth stop may embodied as a generally D-shaped bar (similar to the depth stop 80 of the rasp 50) that has its ends secured to the rasp's cutting head 158. Such a configuration creates a window through which the surgeon can visualize the patient's glenoid surface without the surgeon's line of sight being obstructed by the depth stop.

Figure 15:
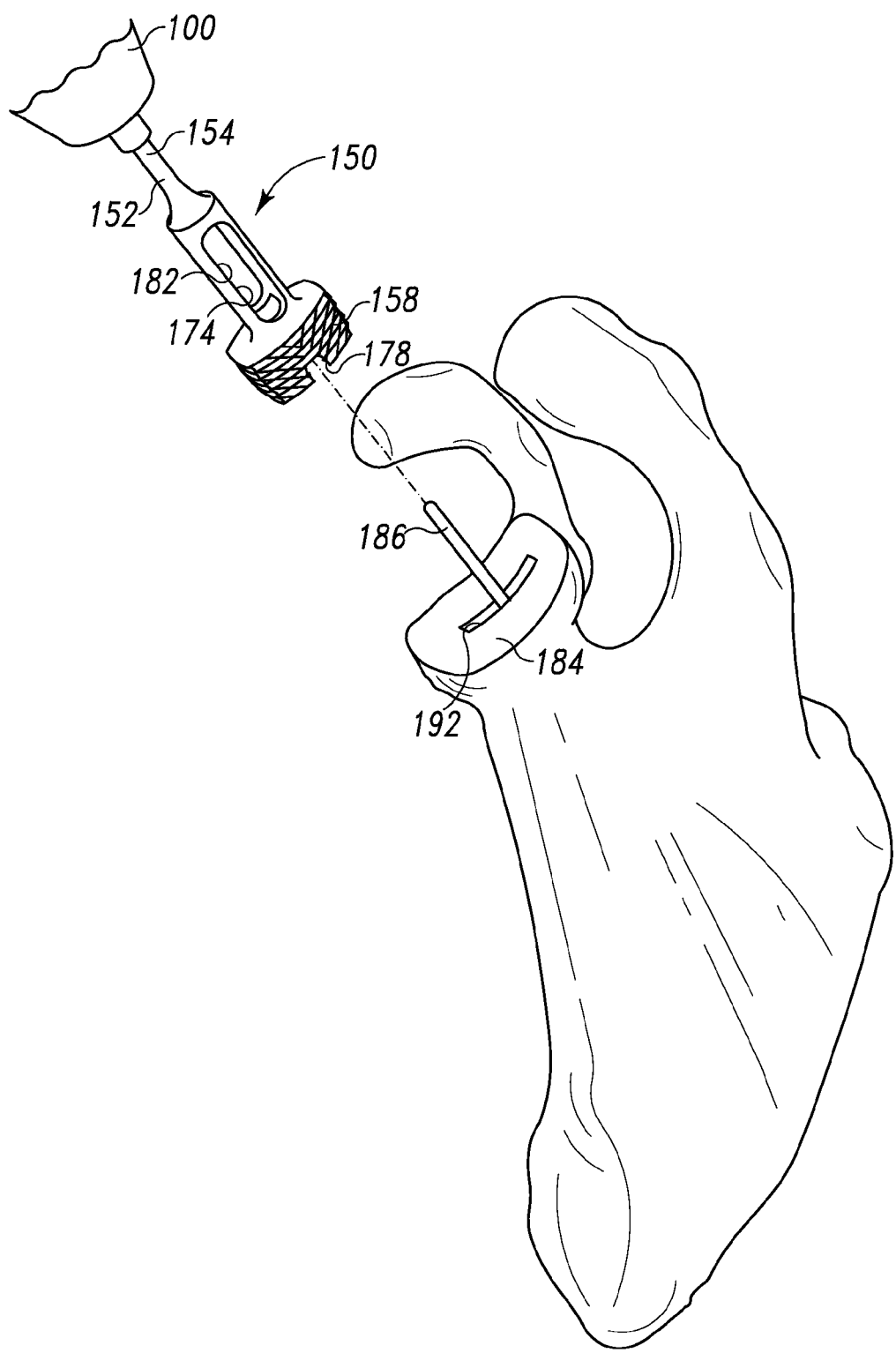
FIG. 15 is a perspective view showing a guide pin inserted in the glenoid of a patient during an orthopaedic surgical procedure to implant the vault glenoid component of FIGS. 10 and 11.
Figure 16:
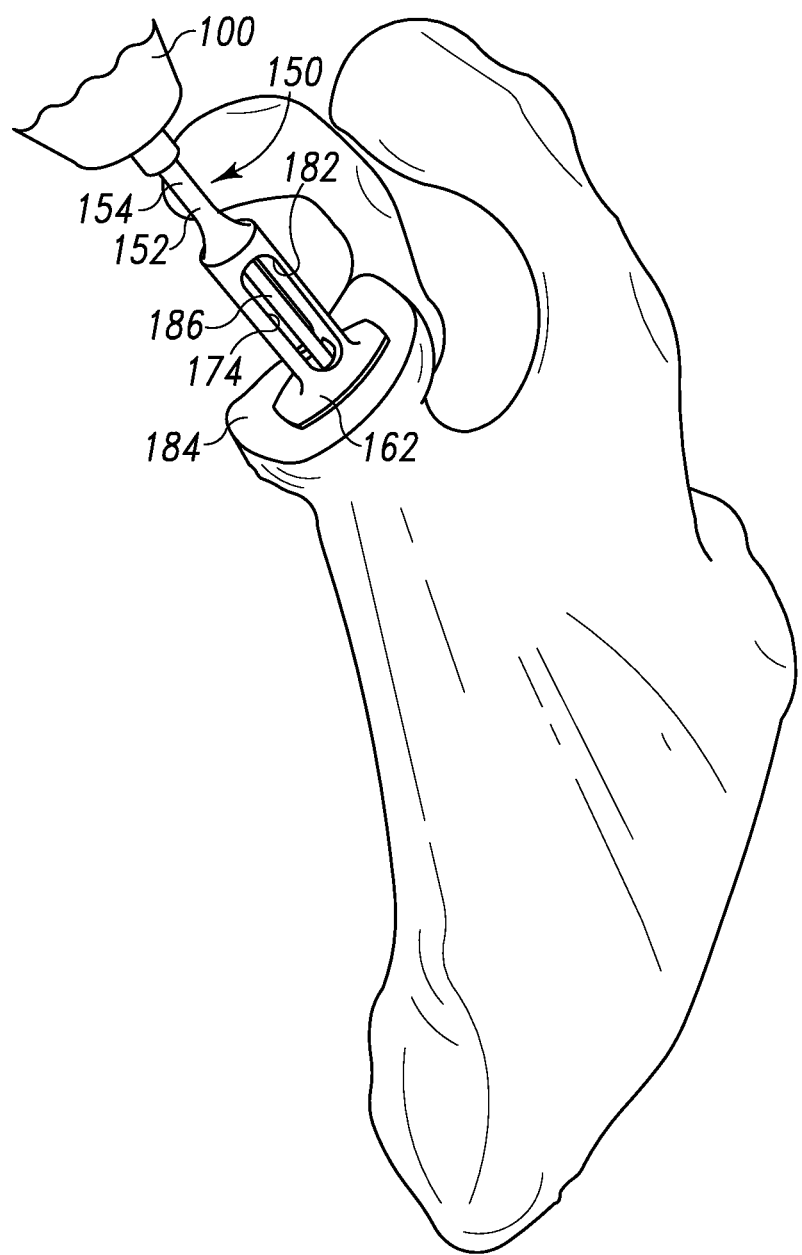
FIG. 16 is a view similar to FIG. 15 showing the reciprocating rasp of FIGS. 12-14 during rasping the patient's glenoid.
Figure 17:
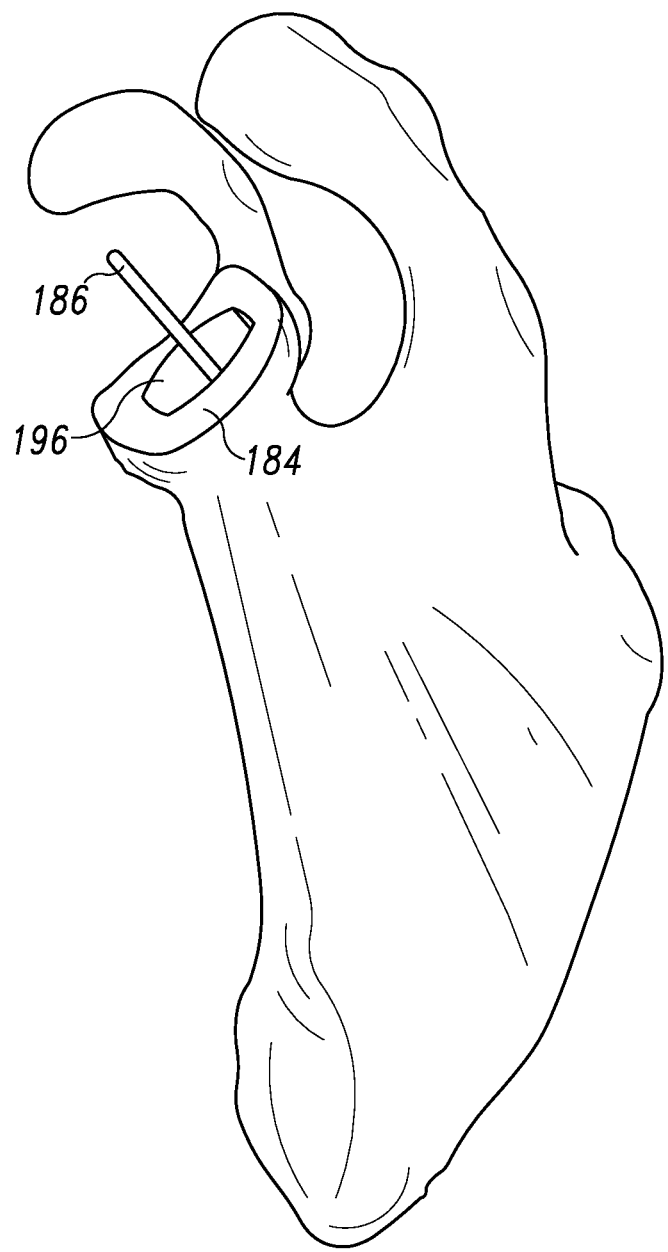
FIG. 17 is a view similar to FIG. 16 showing the patient's glenoid after it has been rasped with the reciprocating rasp of FIGS. 12-14.

Referring now to FIGS. 15-17, there is shown a surgical procedure in which the reciprocating rasp 150 is used to surgically prepare the patient's glenoid 184 for implantation of the vault glenoid component 110. The surgical procedure begins with preoperative planning in which, amongst other things, a CT scan is obtained to plan the placement location and orientation of the vault glenoid component 110. If the vault glenoid component 110 is being implanted as part of a revision procedure, the CT scan may be omitted or substituted for another examination technique. With the preoperative planning complete, the patient's soft tissue is dissected and retracted in order to allow access to the glenoid. Full (i.e., 360°) exposure of the bony glenoid is typically achieved.

As shown in FIG. 15, a guide pin 186 is then inserted in the glenoid 184 in an orientation that will allow for proper placement of the center of the vault glenoid component 110. This can be accomplished using one of a number of different pin placement devices. The guide pin 186 may be scored in locations along its length to allow for controlled breakage to adjust the length of the pin 186 subsequent to being inserted. Specifically, at any point in the procedure, the guide pin 186 can be shortened to a more desirable length by placing a handle just above a score mark and a needle driver just below the same score mark and bending the pin 186 at the score mark. In the illustrative procedure described herein, two to three inches of the pin 186 protrude laterally from the glenoid.

A vault sizer pin guide (not shown) may then be placed over the guide pin 186 and used determine the optimal size vault glenoid component 110 for the patient's glenoid. The periphery of the vault sizer pin guide defines the boundaries of the glenoid 184 to be prepared to accept the vault glenoid component 110. As such, it can be used as a template for marking these boundaries with either a sterile pen or a bovie. The vault sizer also has formed therein a slot that extends in the superior/inferior direction along the center of the sizer. A pen or bovie may be used to mark the bone using the slot as a template. As will be discussed below, a starter channel will be formed in the bone along the mark created with the slot.

Once the boundaries of the vault glenoid implant 110 and the starter channel location have been marked, the glenoid 184 is surgically prepared. At the outset, a surgical burr or other surgical tool is used to create a channel 192 in the patient's glenoid 184 that extends in the superior/inferior direction and corresponds generally to the width of the lead cutting surface 168 of the cutting head 158 (see FIG. 15). The channel 192 is devoid of the hard subchondral bone on the glenoid 184 and thereby facilitates advancement of the reciprocating rasp 150.

A reciprocating rasp 150 sized to match the selected vault glenoid component 110 is then obtained from a number of differently-sized rasps 150 and used to complete the glenoid preparation. The proximal end 154 of the tapered shaft 152 of the selected reciprocating rasp 150 is then secured within the chuck of the reciprocating power tool 100. Once chucked, the rasp is advanced over the guide pin 186. In particular, the V-shaped notch 178 formed in the rasp's cutting head 158 is advanced over the end of the guide pin 186 so that the guide pin 186 enters the alignment bore 174 where it can be visualized by the surgeon through the viewing windows 182. Advancing the alignment bore 174 over the guide pin 186 aligns the rasp's cutting head 158 with the marked boundaries of the glenoid 184 (i.e., the portion of the glenoid 184 that is to be surgically prepared to accept the vault glenoid component 110). Advancing alignment bore 174 over the guide pin 186 also guides the reciprocating trajectory of the reciprocating rasp 150.

As shown in FIG. 16, once the reciprocating rasp 150 is inserted over the guide pin 186, the surgeon activates the reciprocating power tool 100 and advances the lead cutting surface 168 of the cutting head 158 into contact with the glenoid 184. As the rasp 150 is advanced inwardly toward the patient's glenoid 184, the reciprocating motion of the rasp 150 abrades the bone and continues to remove bone until the lateral surface 162 of the cutting head 158 is substantially flush with the bone of the glenoid 184 remaining outside the marked boundaries (i.e., the bone of the glenoid that is not intended to be removed by the rasp 150). When the lateral surface 162 of the cutting head 158 is flush with the remaining bone in such a manner, the rasping preparation of the glenoid 184 is complete—i.e., the rasped glenoid surface 196 has been completed (see FIG. 17). The reciprocating rasp 150 is then removed from the guide pin 186.

It should be appreciated that in lieu of completing the rasped glenoid surface 196 with a single rasp 150, a number of differently-sized rasps 150 may be used. In particular, a number of progressively larger-sized rasps 150 may be used to produce the desired final size. For example, initial rasping may be performed with a rasp 150 having a relatively small cutting head 158. Thereafter, one or more additional rasps 150 having progressively larger cutting heads 158 may be used to perform subsequent rasping to form a larger cavity of the desired final size.

A bone tamp (not shown) which is sized to mimic the geometry of the selected vault glenoid component 110, is placed over the guide pin 186 and used to compact bone graft into any cavities that remain in the wall of the glenoid vault. Because of its geometry, the bone tamp also functions as a trial vault component. The bone tamp is then removed from the guide pin 186. Thereafter, a pin puller or other instrument (not shown) is used to grasp and remove the guide pin 186.

The vault glenoid component 110 is then inserted into the rasped glenoid surface 196. A glenoid impactor (not shown) is used to seat the component 110 until there is complete contact with the perimeter of the rasped glenoid surface 196.

A drill guide (not shown) is then inserted into the cavity 126 of the implanted vault glenoid component 110. The drill guide is configured to guide the drilling direction with respect to the screw hole 128 formed in the inferior surface 124 of the vault glenoid component 110 and the screw hole 130 formed in the rounded medial surface 120. Once positioned in the cavity 126 of the implanted vault glenoid component 110, the surgeon uses the drill guide to drill pilot holes for both of the two screws to be inserted in the vault glenoid component 110. The drill guide is removed, and a screwdriver is used to insert and seat a bone screw in each of the screw holes 128, 130 thereby securing the vault glenoid component 110 to the bone tissue of the patient's scapula.

A peripheral reamer (not shown) is then used to remove any peripheral bone. This provides clearance for a bearing or prosthetic head to be installed in the implanted vault component 110. Thereafter, either an anatomic trial bearing (not shown) or a metaglene/glenosphere trial combination (not shown) can be inserted into the cavity 126 of the implanted vault glenoid component 110 for trialing purposes. Once a desired fit is achieved, the trial components are removed and a corresponding sized implant bearing or prosthetic head is locked to the implanted vault glenoid component 110.

Figure 18:
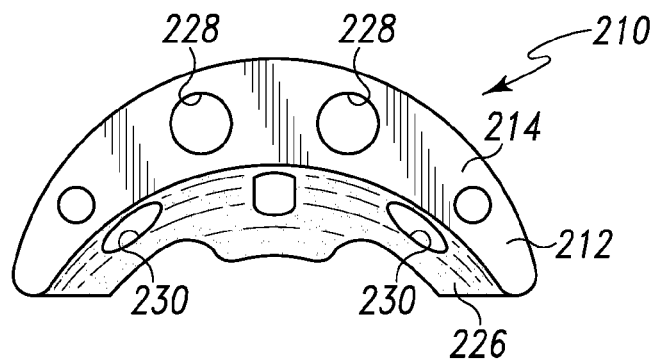
FIG. 18 is a plan view of an acetabular augment component.
Figure 19:
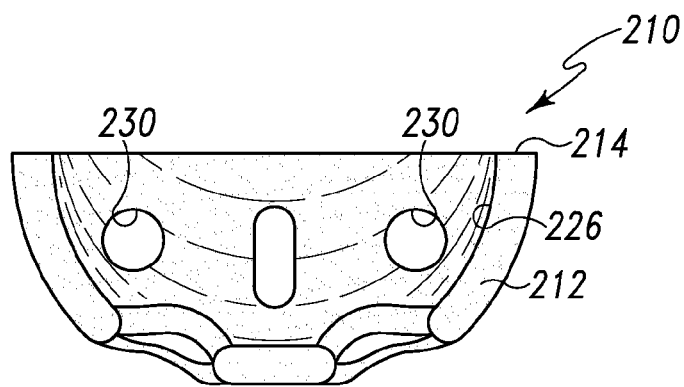
FIG. 19 is a side elevation view of the acetabular augment component of FIG. 18.
Figure 20:
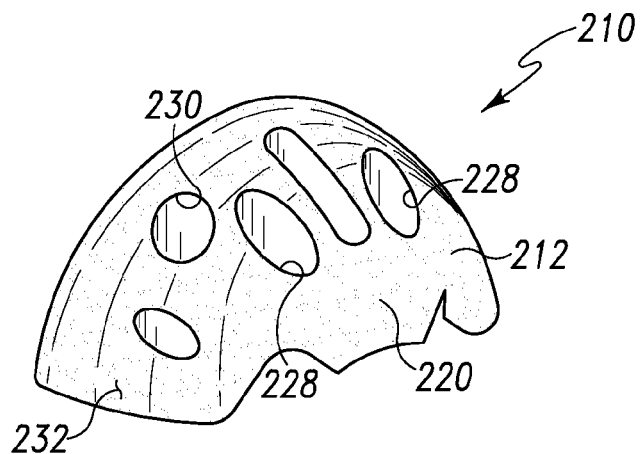
FIG. 20 is a perspective view of the acetabular augment component of FIG. 18.

Referring now to FIGS. 18-20, there is shown an acetabular augment component 210. The acetabular augment component 210 may be implanted into the acetabulum of a patient's hip to replace diseased or degenerated bone tissue to facilitate the implantation of an acetabular cup. As will be discussed in detail below, a number of reciprocating rasps may be used during surgical preparation of the bone tissue to received the acetabular augment component 210.

The acetabular augment component 210 includes a curved metal body 212 having a substantially planar lateral surface 214. The body 212 has curved medial surface 220 that extends from one end of the lateral surface 214 to the other. The body 212 generally forms the shape of a half hemisphere—i.e., it is approximately half the shape of a hemispherically-shaped acetabular cup. The body 212 of the acetabular component 210 has a cavity 226 formed therein. As will be discussed below in more detail, a prosthetic acetabular cup is secured to the acetabular augment component 210 within the cavity 226 once it is implanted in a patient's acetabulum.

A pair of screw holes 228 is formed in the lateral surface 214 of the acetabular augment component 210. The screw holes 228 open into the curved medial surface 220. Another pair of screw holes 230 are likewise formed in the curved medial surface 220 and open into the cavity 226. As will be discussed below in greater detail, bone screws are inserted through the screw holes 228, 230, and thereafter driven into bone tissue to secure the acetabular augment component 210 to the patient's hip bone.

The acetabular augment component 210 is made of an implant grade metal such as stainless steel, cobalt chrome, or titanium, although other metals or alloys may be used. In the illustrative embodiment described herein, the acetabular augment component 210 is embodied as a porous metallic structure. As such, the outer surfaces of the acetabular augment component 210 are porous (i.e., the outer surfaces include a plurality of pores 232), although, in some embodiments, the lateral surface 214 may be smooth. Such porous outer surfaces enhance tissue ingrowth and facilitate the attachment of an acetabular cup to the acetabular augment component 210. In other embodiments, the acetabular augment component 210 may be embodied as a solid metal structure with its outer surfaces having a porous material disposed thereon. Such a porous material may be of the type commonly used in various orthopaedic components to enhance bone tissue ingrowth into the component.

Figure 21:
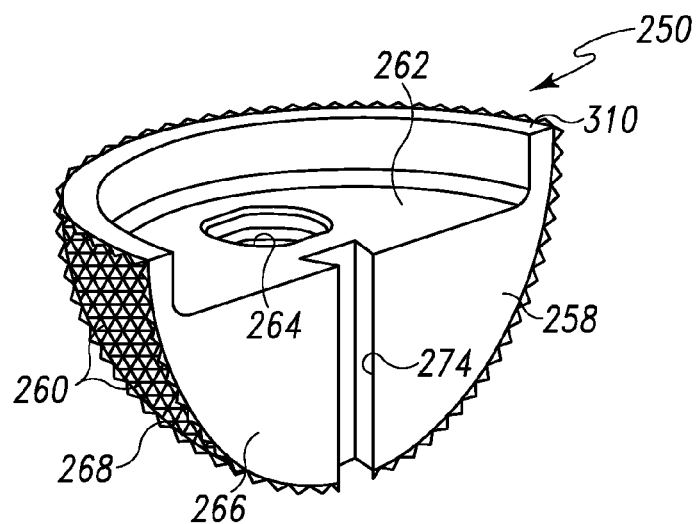
FIG. 21 is a perspective view of a cutting head of a reciprocating rasp for use in an orthopaedic surgical procedure to implant the acetabular augment component of FIGS. 18-20.
Figure 22:
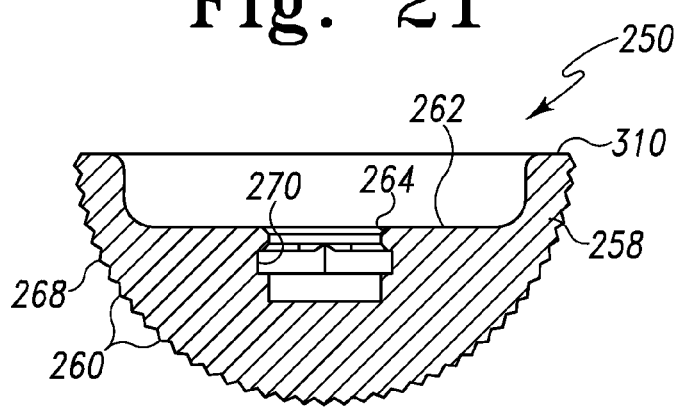
FIG. 22 is cross sectional view of the cutting head of the reciprocating rasp of FIG. 21.
Figure 23:
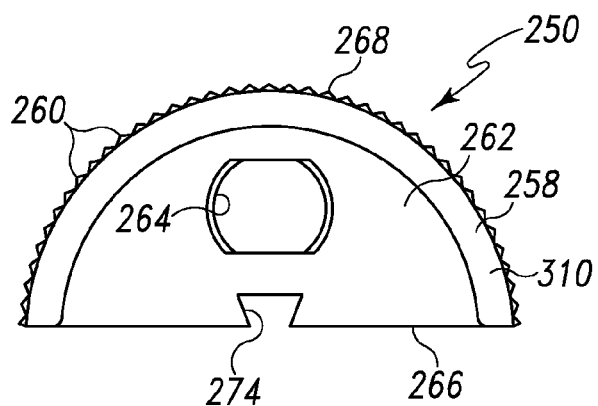
FIG. 23 is a plan view of the cutting head of the reciprocating rasp of FIG. 21.

Referring now to FIGS. 21-23, there is shown a reciprocating rasp 250 that may be used for the surgical preparation of the patient's acetabulum to facilitate implantation of the complex geometry associated with the acetabular augment component 210. The reciprocating rasp 250 includes a cutting head 258 that is coupled to the distal end 256 of a removable shaft 252 (see FIGS. 25 and 26). The shaft 252 may be used as a hand tool, or, alternatively, may have its proximal end 254 secured to the chuck of the reciprocating power tool 100. As will be discussed in greater detail below, the geometry of the cutting head 258 corresponds with the geometry of the acetabular augment component 210. The cutting head 258 of the reciprocating rasp 250 includes a plurality of cutting teeth 260 that are similar in geometry to the cutting teeth 60, 160 of the respective reciprocating rasps 50, 150 described above. When the rasp 250 is advanced into engagement with the acetabulum of the patient's hip bone with reciprocating motion, the cutting teeth 260 of the reciprocating rasp 250 abrade or otherwise cut the bone tissue of the hip bone thereby gradually creating a cavity possessing the geometry (i.e., the shape) required to accept the acetabular augment component 210.

Like the acetabular augment component 210, the cutting head 258 generally forms the shape of a half hemisphere—i.e., it is approximately half the shape of a hemispherically-shaped acetabular cup. The cutting head 258 includes a lateral surface 262 having a posterior surface 266 extending medially therefrom. A curved medial cutting surface 268 that mimics the geometry of the curved medial surface 220 of the acetabular augment component 210 mates with both the lateral surface 262 of the cutting head 258 and its posterior surface 266. The curved medial cutting surface 268 is defined by the outer surfaces of their cutting teeth 260.

The cutting head 258 has a coupling bore 264 defined therein. As can be seen from the cross section of FIG. 22, the coupling bore 264 extends into the body of the cutting head 258 from its lateral surface 262. An annular channel 270 is defined in the cutting head 258 at a location between the lateral surface 262 and the bottom of the coupling bore 264 and hence forms a mid-portion of the coupling bore 264. As will be discussed below, the geometry of the distal end 256 of the removable shaft 252 engages the sidewalls of the annular channel 266 to couple the removable shaft 252 to the cutting head 258.

Like the reciprocating rasps 50, 150 described above in regard to FIGS. 1-17, the reciprocating rasp 250 also includes an alignment member or feature that, as will be discussed below in greater detail, aligns the rasp 250 during a surgical procedure. However, unlike the reciprocating rasps 50, 150 described above in regard to FIGS. 1-17, the reciprocating rasp 250 does not align with a guide pin, but rather a portion of a surgical trial instrument 276 (see FIG. 24). The alignment member or feature may be embodied as any of numerous different structures or features which are configured to coordinate with trial instrument 276 to position the cutting head 258 of the rasp 250 in a desired location relative to the trial instrument. Examples of structures that may function as the alignment member include one or more grooves, tracks, sleeves, rings, cannulated bosses, cylinders, guides, hooks, or any other similar structure capable of receiving a complementary structure or feature formed on the trial instrument.

Figure 24:
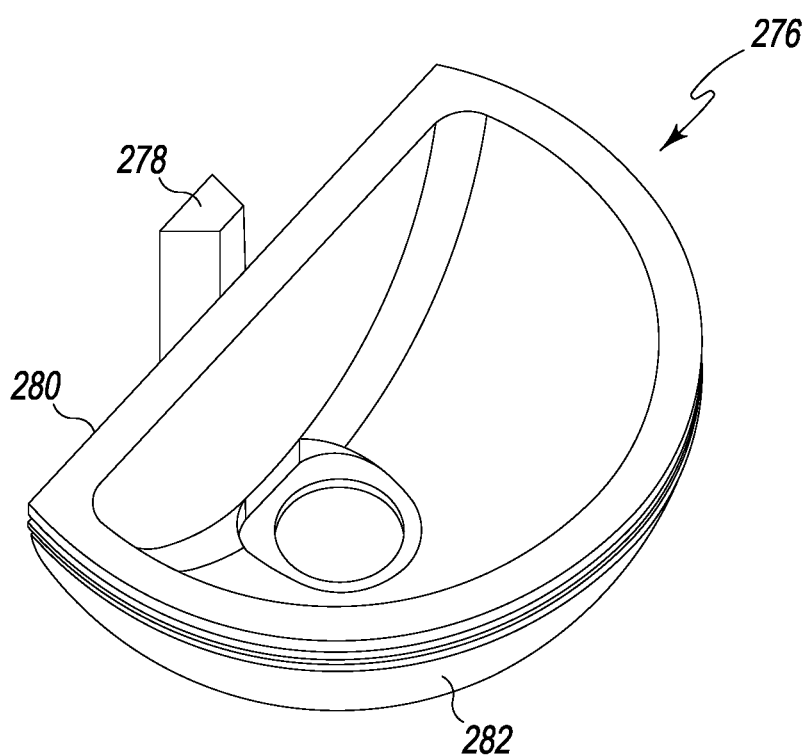
FIG. 24 is a perspective view of a trial instrument used in the performance of a surgical procedure that utilizes the reciprocating rasp of FIGS. 21-23.

In the illustrative embodiment described herein, the alignment member or feature is embodied as an elongated groove 274 that is formed in the posterior surface 266 of the cutting head 258. As can be seen in FIG. 24, the trial instrument 276 includes an elongated tongue 278 formed in its anterior surface 280. During rasping of the patient's acetabulum, the tongue 278 is positioned in the groove 274 of the rasp 250 thereby establishing and maintaining the alignment of the rasp. Unlike traditional hemispherically-shaped trial acetabular instruments, the trial instrument 276 includes a body having the shape of a partial hemisphere. In other words, it approximates the shape of a blunted hemispherically-shaped trial. As such, its anterior surface 280 is planar with the tongue 278 extending therefrom. A curved outer surface 282 mates with the anterior surface 280. The curvature of the outer surface 282 is hemispherical—i.e., the outer surface defines a true hemisphere that has been intersected by a plane (the plane being the anterior surface 280).

Referring now to FIGS. 25 and 26, the removable shaft 252 is shown in greater detail. The shaft 252 has a handle 284 that is gripped by a surgeon during manipulation of the rasp 250. A release lever 286 is positioned near the handle 284 and is used by the surgeon to selectively couple one of the cutting heads 258 to the shaft 252. In particular, the release lever 286 is mechanically coupled to an elongated pin 288 that extends through a bore 290 defined in the shaft. The pin 288 has a tapered distal end 292 that engages the distal end 256 of the shaft 252. The distal end 256 of the shaft 252 is defined by a pair of opposing jaws 294. The inner surfaces 296 of the jaws 294 are tapered at an angle that corresponds with the geometry of the tapered distal end 292 of the pin 288. As such, when fully extended, the tapered distal end 292 engages the tapered inner surfaces 296 of the jaws 294 thereby urging the jaws 294 outwardly away from one another. However, when the release lever 286 is depressed, the pin 288 is retracted (i.e., its distal end 292 is moved in the direction away from the distal end 256 of the shaft 252), thereby allowing the jaws 294 to be deflected or otherwise moved inwardly toward one another. In particular, when the pin 288 is retracted, its tapered distal end 292 disengages the tapered inner surfaces 296 of the jaws 294 thereby allowing the jaws 294 to deflect inwardly toward the center of the shaft.

Figure 27:
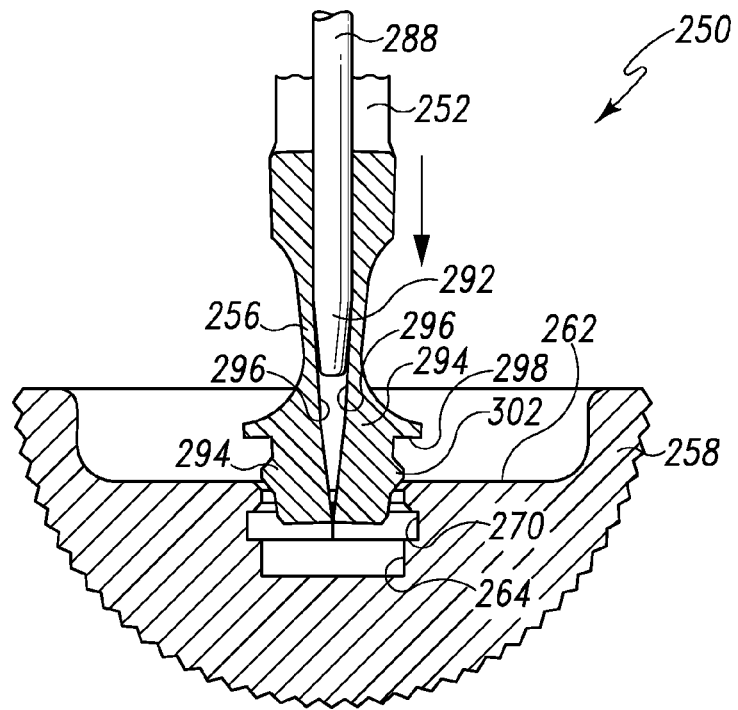
FIGS. 27 and 28 are cross sectional views showing the removable shaft being coupled to the cutting head of the reciprocating rasp, note the pin of the removable shaft is not shown in cross section for clarity of description.

As shown in FIG. 27, with the release lever 286 depressed, the shaft 252 may be advanced into the coupling bore 264 of the cutting head 258 of the rasp 250. Because the pin 288 is retracted, the jaws 294 of the distal end 256 of the shaft 252 are permitted to deflect toward one another and hence enter the coupling bore 264. Once a depth stop 298 formed on the distal end 256 of the shaft 252 contacts the lateral surface 262 of the cutting head 258, the surgeon releases the release lever 286.

When the release lever 286 is released, the pin 288 is extended thereby causing its tapered distal end 292 to engage the tapered inner surfaces 296 of the jaws 294. This urges the jaws 294 outwardly away from one another thereby causing an annular ring 302 formed on the outer surface of the jaws 294 to be received into the annular channel 270 of the cutting head's coupling bore 264. When positioned in its fully extended position, the tapered distal end 292 prevents the inner surfaces 296 of the jaws 294 from moving inwardly thereby locking the removable shaft 252 to the cutting head 258. It should be appreciated that the shaft 252 may be subsequently removed by the surgeon by pressing the release lever 286 to allow the jaws 294 to retract when the shaft 252 is pulled away from the cutting head 258.

As described above, the removable shaft 252 may be quickly coupled to, and decoupled from, various cutting heads 258 (or even other surgical instruments). As will be discussed below, such a feature allows a number of different cutting heads 258 to be used in a progressive rasping technique.

Referring now to FIGS. 29-34, there is shown a surgical procedure in which the reciprocating rasp 250 is used to surgically prepare the patient's acetabulum 304 for implantation of the acetabular augment component 210. The surgical procedure begins with preoperative planning in which, amongst other things, a number of X-ray images are obtained to plan the placement location and orientation of the acetabular augment component 210. If the acetabular augment component 210 is being implanted as part of a revision procedure, the use of X-rays may be omitted or substituted for another examination technique. With the preoperative planning complete, the patient's soft tissue is dissected and retracted in order to allow access to the acetabulum 304. Full (i.e., 360°) exposure of the bony acetabulum is typically achieved.

A sizer guide or other similar instrument is then used to determine the appropriate size of acetabular implant (i.e., cup) to be implanted. In the exemplary procedure described herein, implantation of a 62 mm acetabular cup (and associated 62 mm acetabular augment component) will be illustrated. Such components have a 62 mm outer diameter (i.e., a 62 mm OD). It should be appreciated that the surgical procedure for other sizes of implants is performed in essentially the same manner.

Figure 29:
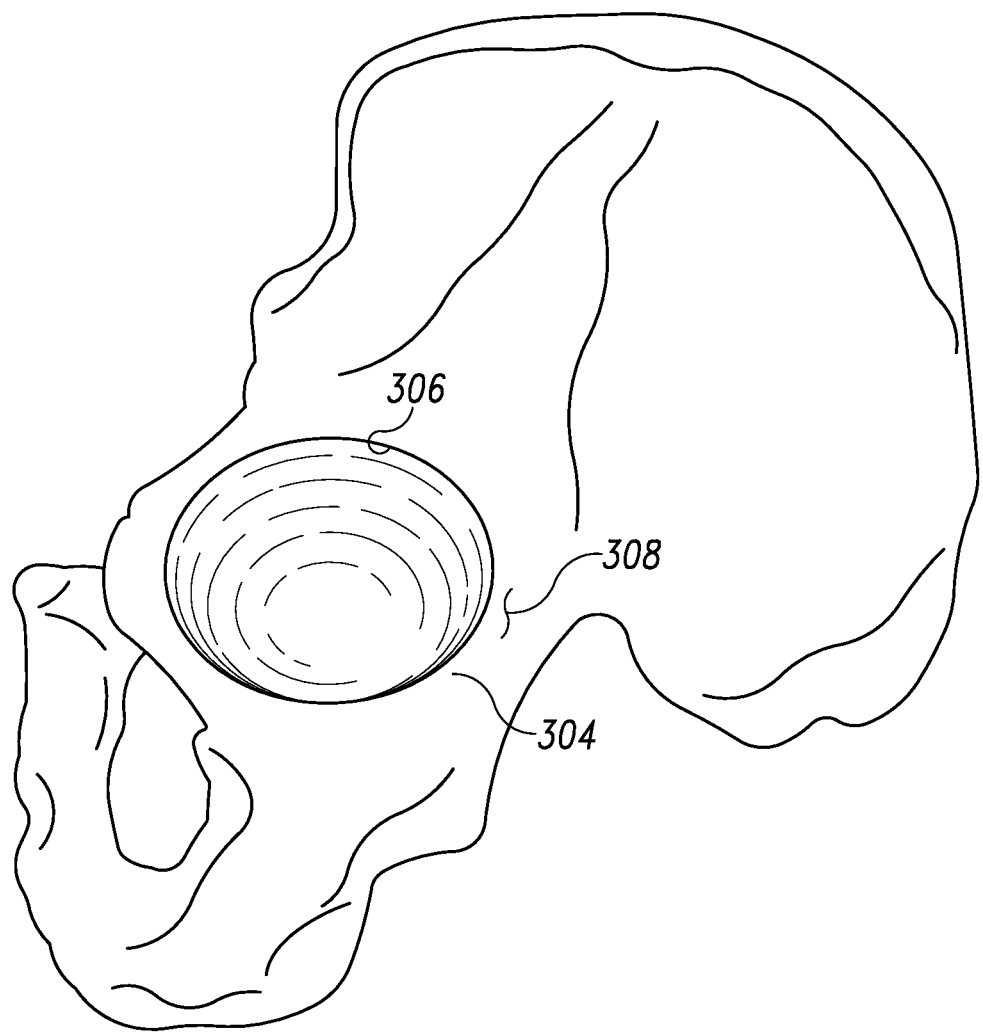
FIG. 29 is a perspective view showing the acetabulum of a patient after it has been reamed with a spherical reamer during an orthopaedic surgical procedure to implant the acetabular augment component of FIGS. 18-20.

Once the final implant size is determined, the patient's acetabulum is reamed in a typical manner. In particular, a spherical reamer (not shown) is used to ream the acetabular surface of the patient's hip bone to create hemispherically-shaped reamed surface 306 as shown in FIG. 29. In the case of implantation of a 62 mm acetabular cup, a 61 mm spherical reamer is used (i.e., a reamer with a 61 mm OD). This reamed surface 306 is the final surgically-prepared surface that contacts a portion of the acetabular cup when it is implanted.

Figure 30:
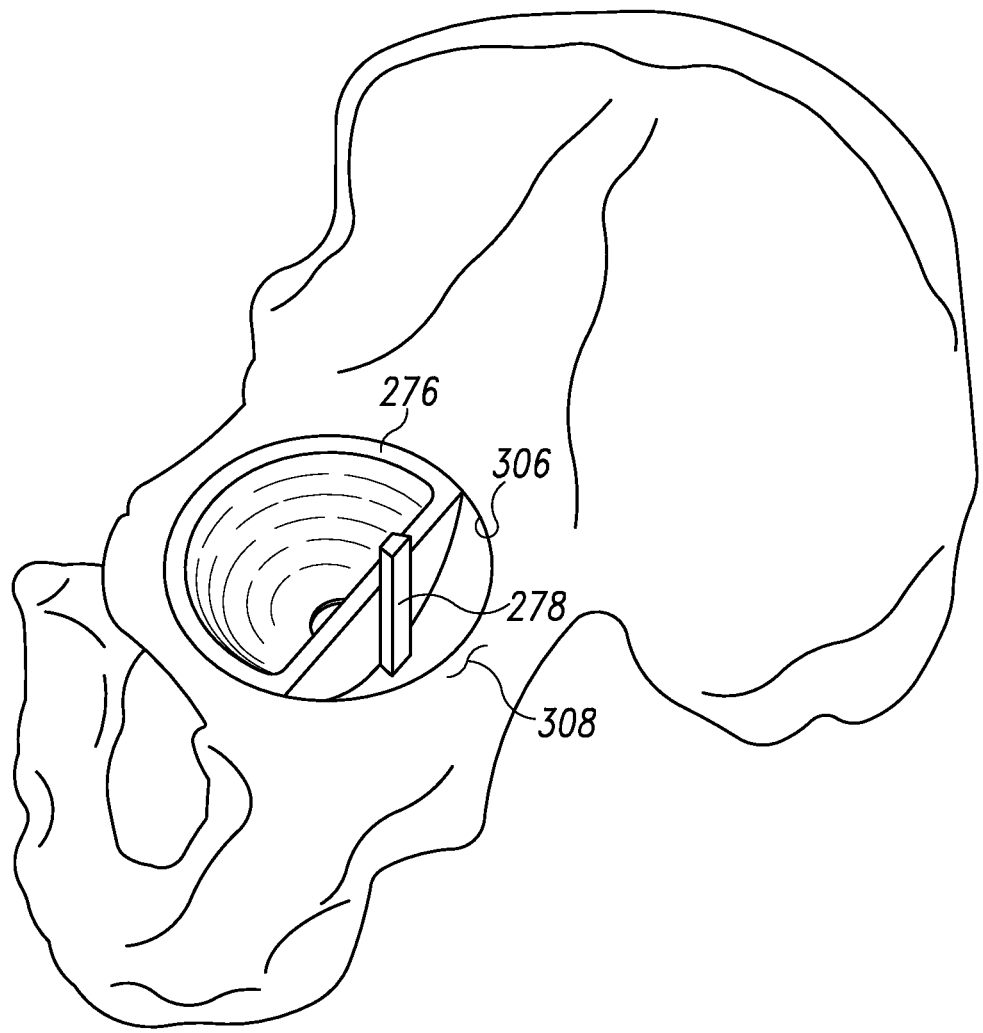
FIG. 30 is a view similar to FIG. 29 showing the trial instrument of FIG. 24 inserted into the patient's reamed acetabulum.

As shown in FIG. 30, an appropriately sized trial instrument 276 is then inserted into the reamed surface 306. In the exemplary case of implantation of a 62 mm acetabular cup described herein, a 61 mm trial instrument 276 is used (i.e., a trial instrument with a 61 mm OD). As can be seen in FIG. 30, the trial instrument 276 is positioned in the reamed surface 306 in an orientation in which the instrument's elongated tongue 278 faces the general direction of the diseased or deteriorated bone tissue 308 of the hip bone (i.e., the bone tissue that is to be removed and replaced with the acetabular augment component 210).

Figure 28:
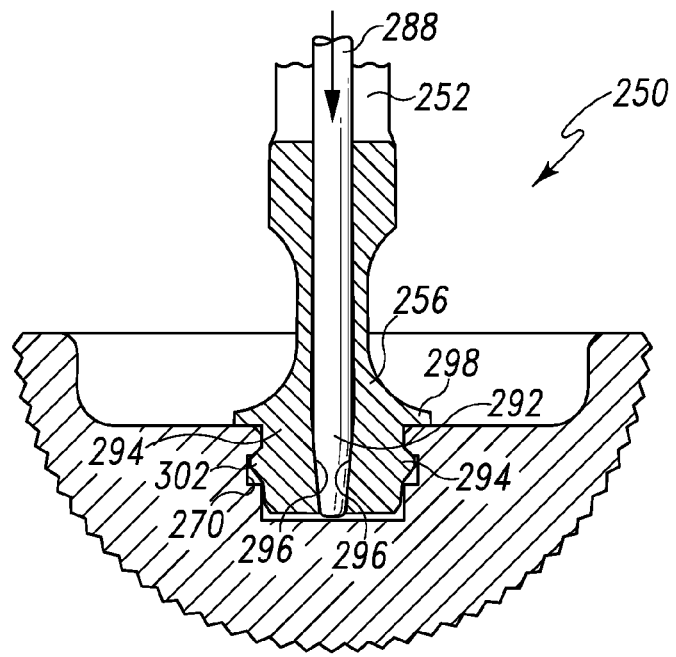
Figure 31:
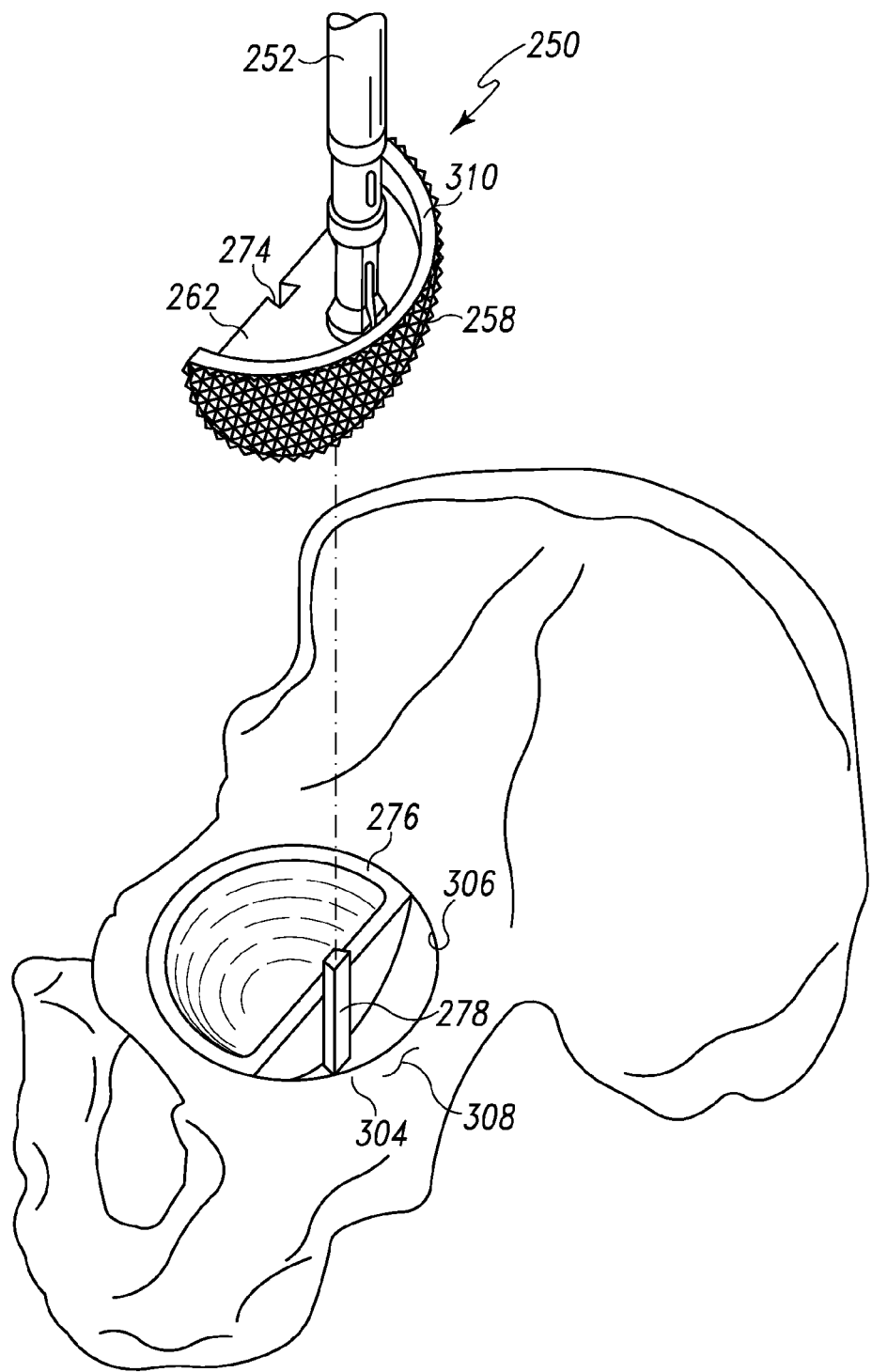
FIGS. 31 and 32 are views similar to FIG. 29 showing the reciprocating rasp of FIGS. 21-23 during rasping of the patient's acetabulum.

As shown in FIG. 31, the reciprocating rasp 250 is then used to remove the diseased or deteriorated bone tissue 308 of the hip bone. To do so, a number of progressively larger-sized cutting heads 258 are used until the desired final size is achieved. For example, in the exemplary case of implantation of a 62 mm acetabular augment component 210 described herein, initial rasping is performed with a 50 mm cutting head 258 (i.e., a cutting head with a 50 mm OD). To do so, the surgeon first secures the 50 mm cutting head 258 to the removable shaft 252 by pressing the release lever 286 and inserting the jaws 294 of the distal end 256 of the shaft into the coupling bore 264 of the 50 mm cutting head 258 in the manner described above in regard to FIGS. 27 and 28. With the 50 mm cutting head 258 coupled to the shaft 252, the surgeon then advances the rasp 250 toward the trial instrument 276 positioned in the reamed surface 306. The surgeon positions the rasp 250 such that the elongated tongue 278 formed in the anterior surface 280 of the trial instrument 276 is received into the groove 274 of the 50 mm cutting head 258 thereby establishing and maintaining alignment of the rasp 250 relative to the trial instrument 276.

Figure 32:
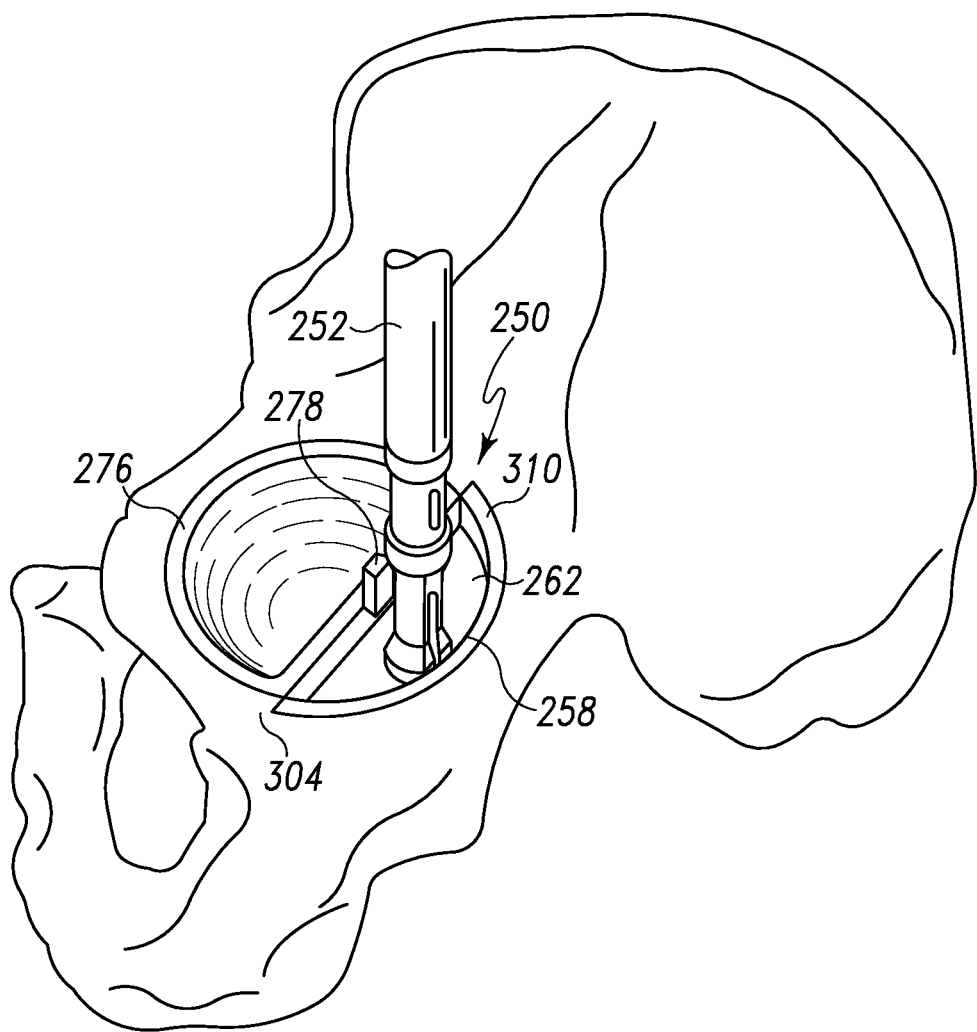

Once the elongated tongue 278 is received into the groove 274 of the 50 mm cutting head 258, the surgeon activates the reciprocating power tool 100 (if the rasp 250 is being powered by the power tool 100 as opposed to manual operation of the shaft 252 via its handle 284) and advances the lead cutting surface of the 50 mm cutting head 258 into contact with the patient's acetabulum 304. As shown in FIG. 32, as the rasp 250 is advanced inwardly toward the patient's acetabulum 304, the reciprocating motion of the rasp 250 abrades the bone and continues to remove bone until the upper edge 310 of the lateral surface 262 of the cutting head 258 is substantially flush with the bone of the patient's acetabulum 304 remaining outside of the rasped surface (i.e., the bone of the acetabulum that is not intended to be removed by the rasp 250). When the upper edge 310 of the lateral surface 262 of the cutting head 258 is flush with the remaining bone in such a manner, the rasping preparation of the acetabulum 304 with the 50 mm cutting head 258 is complete.

Figure 33:
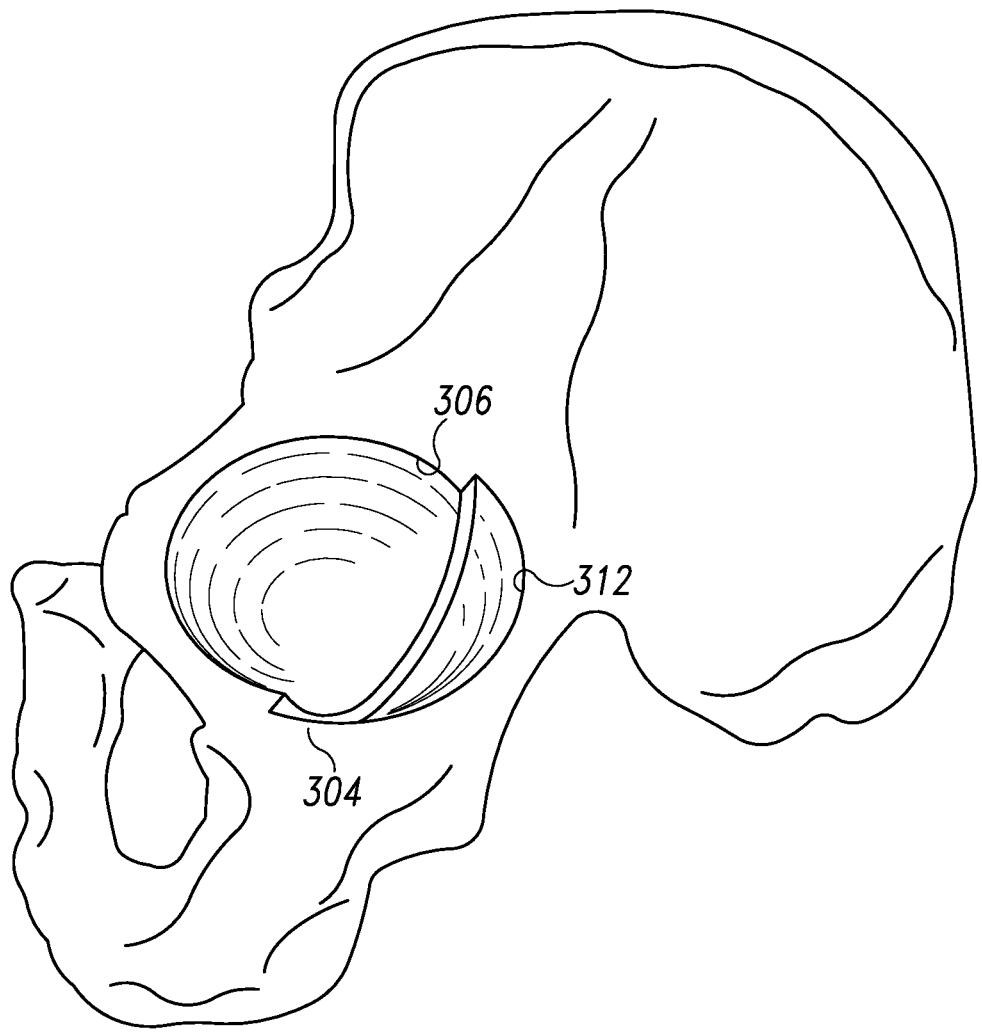
FIG. 33 is a view similar to FIG. 29 showing the patient's acetabulum after it has been rasped with the reciprocating rasp of FIGS. 21-23.
Figure 34:
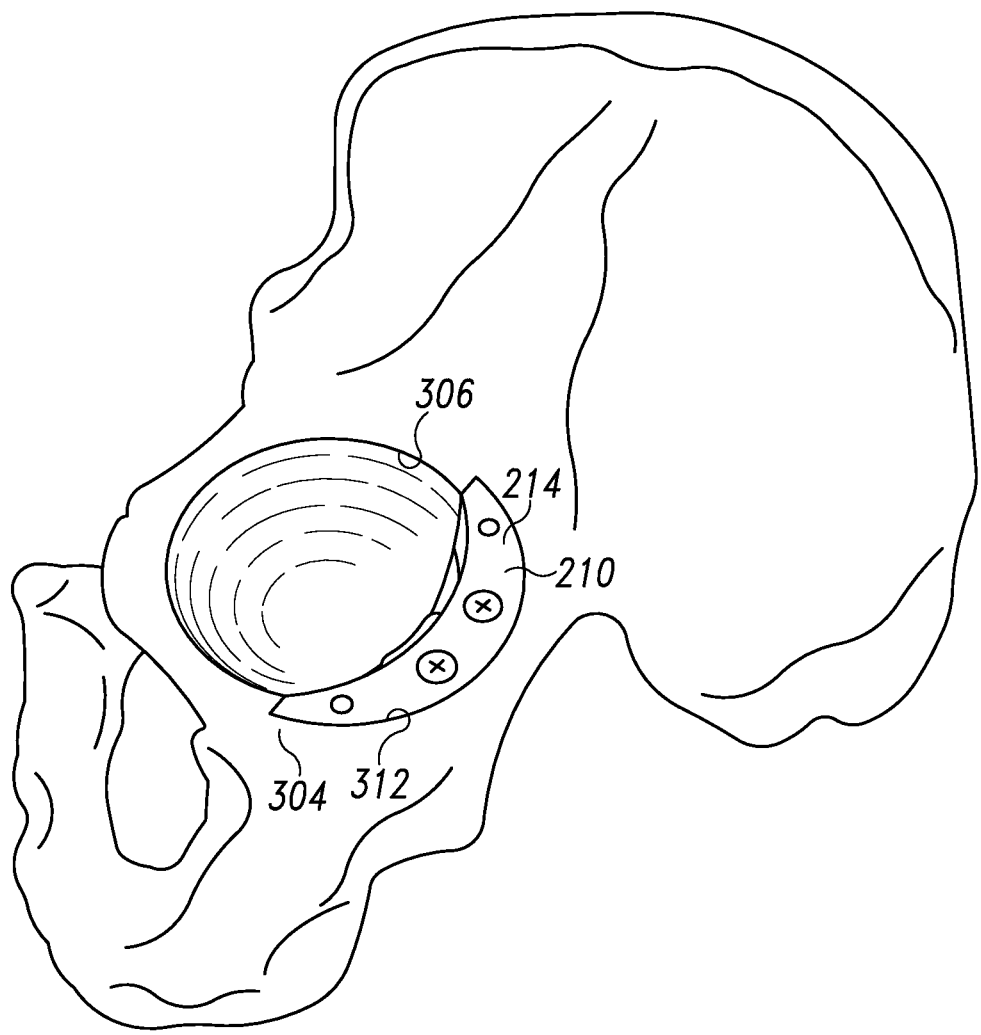
FIG. 34 is a view similar to FIG. 29 showing the acetabular augment component implanted in the patient's acetabulum.

The 50 mm cutting head 258 is then separated from the trial instrument 276 and decoupled from the removable shaft 252. Thereafter, a 54 mm cutting head 258 is secured to the removable shaft 252 and the rasping procedure is repeated. The rasping procedure is then performed again with a 58 mm cutting head, and finally with a 62 mm cutting head. Once done, a prepared augment surface 312 of the desired size (i.e., 62 mm in the exemplary case described herein) has been formed, as shown in FIG. 33.

Once the bone has been prepared in such a manner, the acetabular augment component 210 is then implanted. In the exemplary procedure described herein, a 62 mm acetabular augment component 210 is first positioned in the prepared augment surface 312 in the desired position. The acetabular augment component 210 may be temporarily pinned in place by inserting pins (not shown) through a pair of pin holes 314 formed in the component 210 (see FIGS. 18 and 19). Once pinned in place, the acetabular augment component 210 is screwed to the patient's hip bone. In particular, bone screws are inserted through the screw holes 228, 230 formed in the acetabular augment component 210 and thereafter driven into the surrounding bone tissue. The pins may then be removed. The implanted acetabular augment component 210 is shown fully implanted in FIG. 34.

Once the 62 mm acetabular augment component 210 has been implanted, a 62 mm acetabular cup (not shown) may then be implanted. The acetabular cup is positioned in the hemispherically-shaped cavity formed by the reamed surface 306 of the patient's acetabulum 304 and the acetabular augment component 210. The acetabular cup may be secured to the surrounding bone tissue with bone screws and/or cement. Bone cement may also be used to secure the acetabular cup to the acetabular augment component 210. Moreover, screws may be inserted through the acetabular cup and driven into a self-tapping slot 316 formed in the acetabular augment component 210. This completes implantation of the acetabular cup.

It should be appreciated that the reciprocating rasp 250 may take on different forms. For example, in lieu of a removable shaft 252, each of the cutting heads 258 may be embodied with a shaft secured thereto in a similar manner to the rasps 50, 150. The cutting head 258 may also be embodied with a depth stop that bottoms out on the trial instrument 276 or other structure when the rasp 250 has reached a desired depth. Moreover, the location of the alignment features of the trial instrument 276 and the cutting head 258 may be interchanged. For example, the groove may be formed in the trial instrument 276, with the tongue being formed on the cutting head 258.

The surgical procedure may also be altered such that fewer or more rasps are used. For example, in lieu of 2 mm increments, 4 mm increments may be used. Other increments may also be used. In some cases, a single rasping of the desired final size may be performed.

Figure 35:
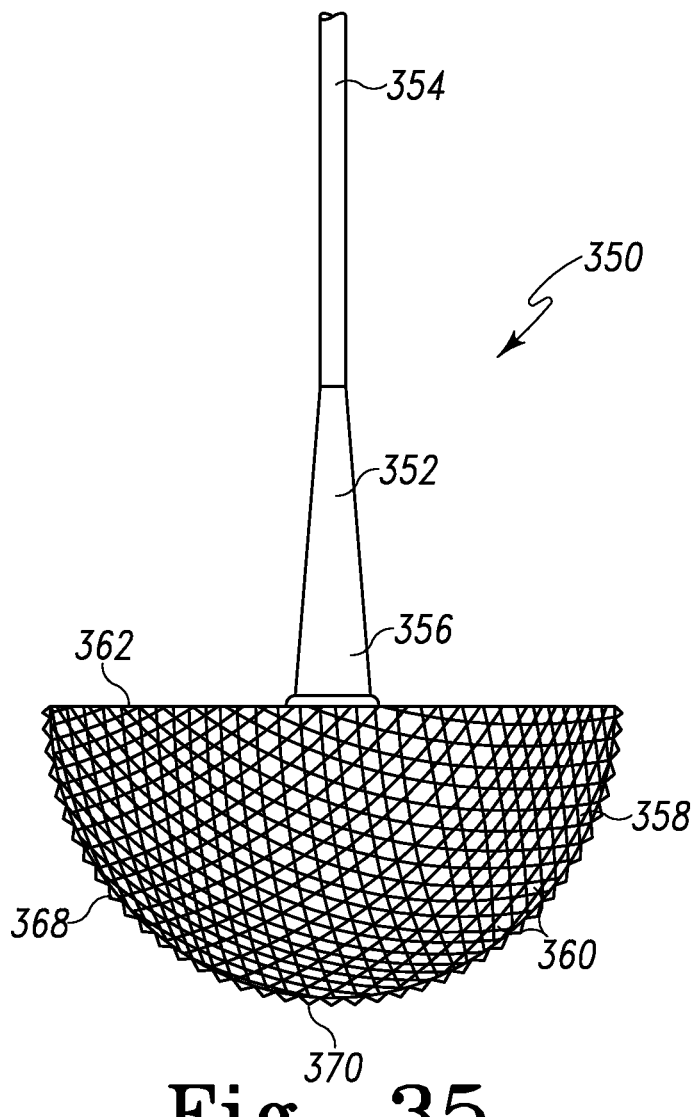
FIG. 35 is a plan view of another reciprocating rasp for use in an orthopaedic surgical procedure to implant the acetabular augment component of FIGS. 18-20.
Figure 36:
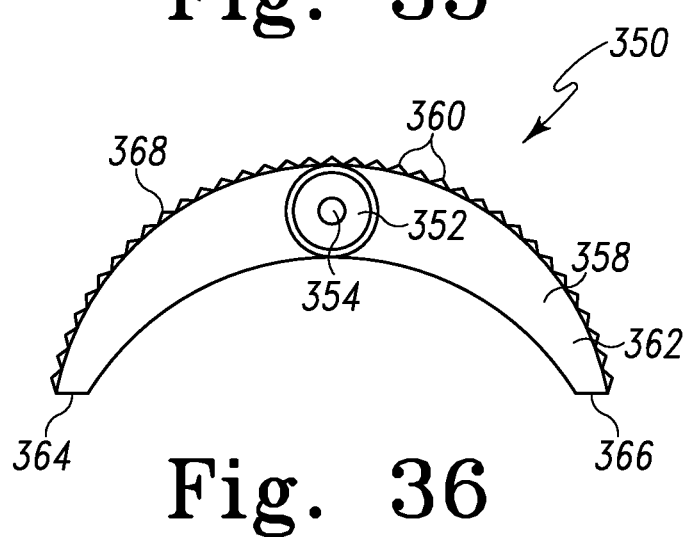
FIG. 36 is a side elevation view of the reciprocating rasp of FIG. 35.

Another embodiment of a reciprocating rasp 350 that may be used for the surgical preparation of the patient's acetabulum to facilitate implantation of the acetabular augment component 210 is shown in FIGS. 35 and 36. As will be discussed below in more detail, the reciprocating rasp 350 is designed as a finishing tool to form the final surgical surface, with some of the initial bone removal being performed with other instruments. The reciprocating rasp 350 includes a cutting head 358 that is coupled to the distal end 356 of a shaft 352. The shaft 352 has a proximal end 354 that may be secured to the chuck of the reciprocating power tool 100. As will be discussed in greater detail below, the geometry of the cutting head 358 corresponds with the geometry of the acetabular augment component 210. The cutting head 358 of the reciprocating rasp 250 includes a plurality of cutting teeth 360 that are similar in geometry to the cutting teeth 60, 160, 260 of the respective reciprocating rasps 50, 150, 250 described above. When the rasp 350 is advanced into engagement with the acetabulum of the patient's hip bone with reciprocating motion, the cutting teeth 360 of the reciprocating rasp 350 abrade or otherwise cut the bone tissue of the hip bone thereby creating a finished cavity possessing the geometry (i.e., the shape) required to accept the acetabular augment component 210.

The cutting head 358 is generally seashell-shaped and approximates the backside geometry of the acetabular augment component 210. As such, the cutting head 358 is generally D-shaped when viewed from above (see FIG. 35). The cutting head 358 includes a lateral surface 362 having an anterior surface 364 and a posterior surface 366 extending medially therefrom. A curved medial cutting surface 368 that mimics the geometry of the curved medial surface 220 of the acetabular augment component 210 extends medially away from the lateral surface 362 of the cutting head 358 and mates with the anterior surface 364 and the posterior surface 366 at lead cutting surface 370. The curved medial cutting surface 368 is defined by the outer surfaces of its cutting teeth 360. As shown in FIG. 36, when viewed from the side, the lateral surface 362 of the cutting head 358 is generally C-shaped. Since the lead cutting surface 370 is generally linear, the curved medial surface 368 forms a tapered surface when viewed from the side.

Like the other rasps described herein, the reciprocating rasp 350 may be made of any suitable material, including medical-grade metals. In addition, since it is primarily a finishing tool, the reciprocating rasp 350 may be made from a rigid polymer such as polyaryetheretherketone (PEEK). In such a configuration, the rasp 350 may be used as a disposable instrument.

Figure 37:
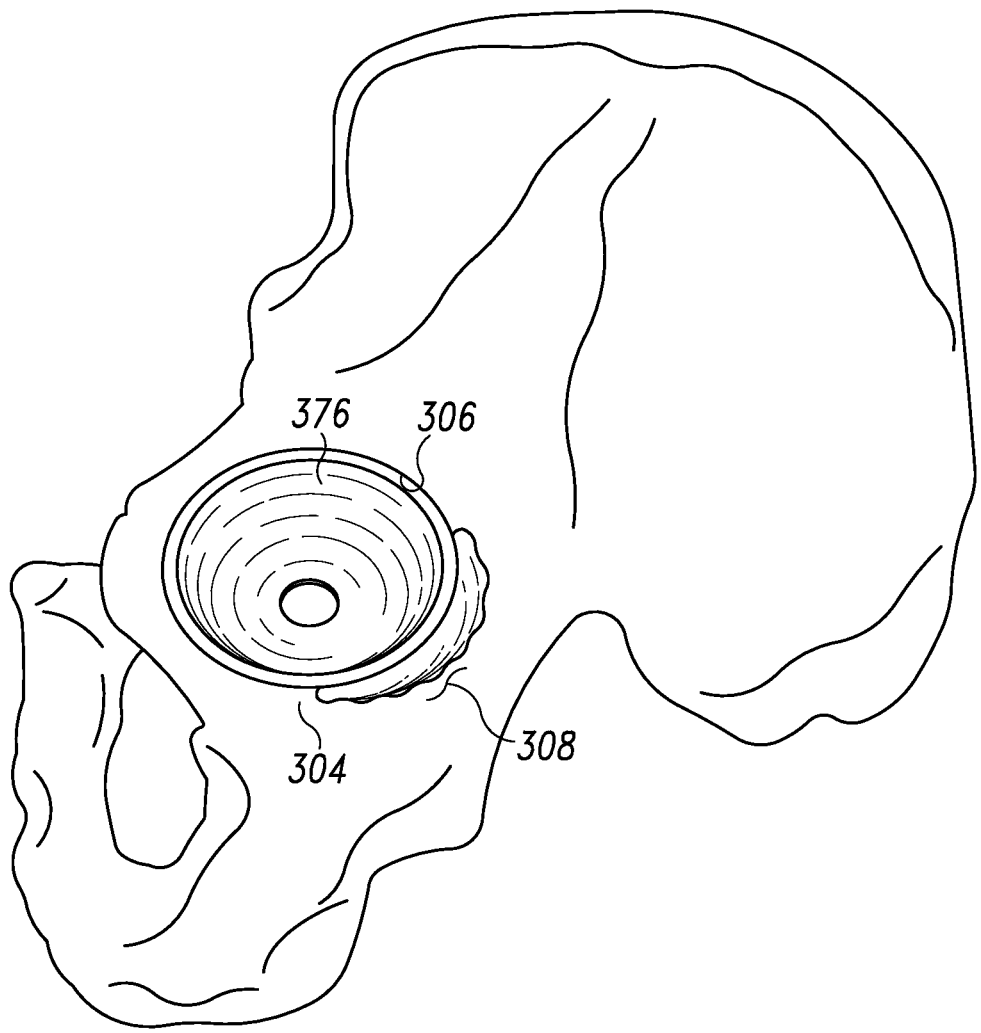
FIG. 37 is a perspective view showing the acetabulum of a patient after it has been reamed with a spherical reamer during an orthopaedic surgical procedure to implant the acetabular augment component of FIGS. 18-20, note a trial instrument has been inserted into the reamed acetabulum.
Figure 38:
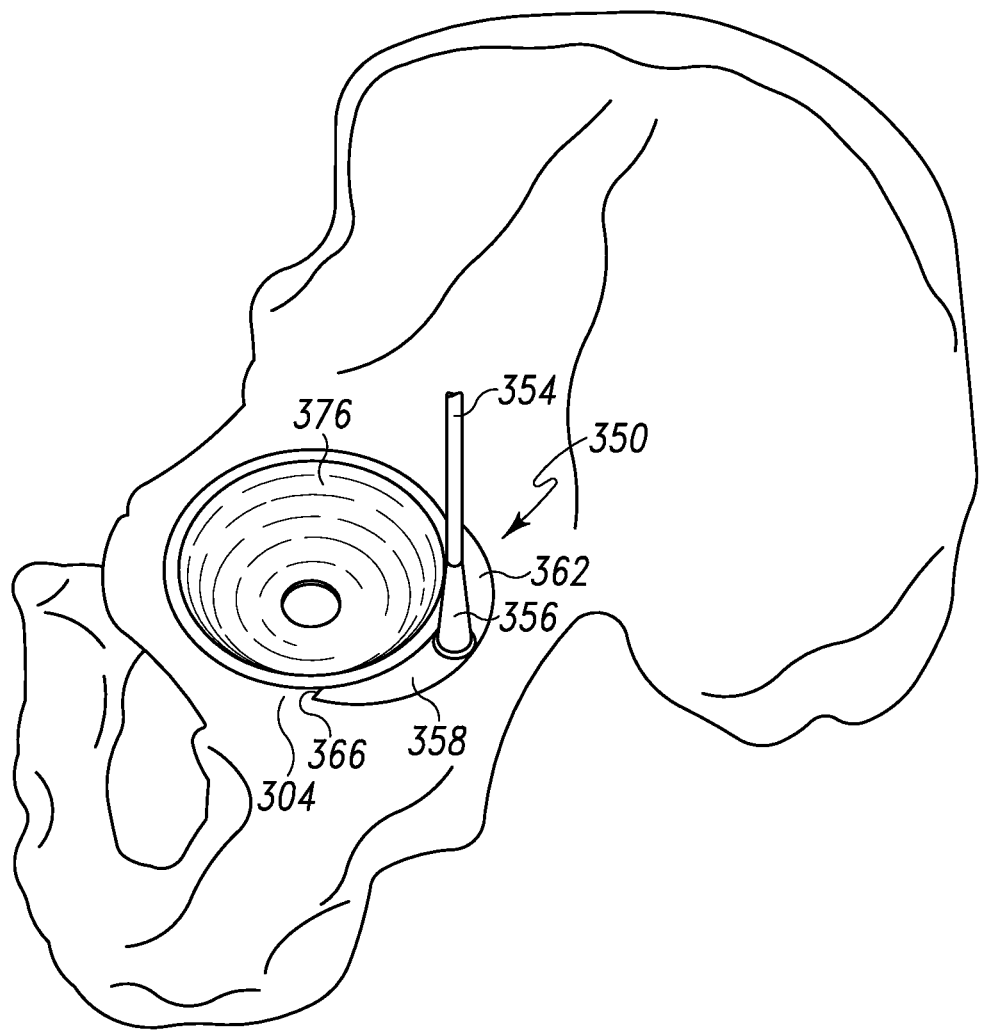
FIG. 38 is a view similar to FIG. 37 showing the reciprocating rasp of FIGS. 35 and 36 during rasping or the patient's acetabulum.

Referring now to FIGS. 37-38, there is shown a surgical procedure in which the reciprocating rasp 350 is used to surgically prepare the patient's acetabulum 304 for implantation of the acetabular augment component 210. The surgical procedure is essentially the same as the surgical procedure shown in FIGS. 29-34 except for the formation of the prepared augment surface 312. As such, the preoperative procedure and reaming procedure is the same and produces a reamed surface 306 similar to as shown in FIG. 29. However, in lieu of the trial instrument 276 of FIG. 30, a traditional (i.e., hemisphereically-shaped) acetabular trial instrument 376 is inserted into the reamed surface 306, as shown in FIG. 37. In the exemplary case of implantation of a 62 mm acetabular cup described herein, a 61 mm trial instrument 376 is used (i.e., a traditional trial instrument with a 61 mm OD).

The surgeon then uses a surgical burr or other instrument (not shown) to perform an initial, "rough" removal of the diseased or deteriorated bone tissue 308 of the hip bone (i.e., the bone tissue that is to be removed and replaced with the acetabular augment component 210). As can be seen in FIG. 37, after such burring, the diseased or deteriorated bone tissue 308 proximate to the finished surface remains for removal by the reciprocating rasp 350.

As shown in FIG. 38, the reciprocating rasp 350 is then used to remove the remainder of the diseased or deteriorated bone tissue 308 of the hip bone. To do so, a rasp 350 with an appropriately-sized cutting head 358 is placed in the chuck of the reciprocating power tool 100. For example, in the exemplary case of implantation of a 62 mm acetabular augment component 210 described herein, a reciprocating rasp with a 62 mm cutting head 358 (i.e., a cutting head with a 62 mm OD) is used. As shown in FIG. 38, anterior surface 364 and the posterior surface 366 of the cutting head 358 are positioned in contact with the outer surface of the trial instrument 376. During rasping, the anterior surface 364 and the posterior surface 366 remain in contact with the outer surface of the trial instrument 376. In such a way, the trial instrument's outer surface functions as an alignment feature for guiding the rasp 350 during bone removal.

The surgeon then activates the reciprocating power tool 100 and advances the lead cutting surface 370 of the cutting head 358 into contact with the patient's acetabulum 304. As shown in FIG. 38, as the rasp 350 is advanced inwardly toward the patient's acetabulum 304, the reciprocating motion of the rasp 350 abrades the bone and continues to remove bone until the lateral surface 362 of the cutting head 358 is substantially flush with the bone of the patient's acetabulum 304 remaining outside of the rasped surface (i.e., the bone of the acetabulum that is not intended to be removed by the rasp 350). When the lateral surface 362 of the cutting head 358 is flush with the remaining bone in such a manner, the rasping preparation of the acetabulum 304 is complete and hence a prepared augment surface 312 of the desired size (i.e., 62 mm in the exemplary case described herein) has been formed. The prepared augment surface 312 formed by the reciprocating rasp 350 is similar to as shown in FIG. 33.

Once the bone has been prepared in such a manner, the acetabular augment component 210 is then implanted in a manner similar to as described above in regard to FIGS. 33 and 34. Thereafter, acetabular cup is implanted in a similar to as described above.

Figure 39:
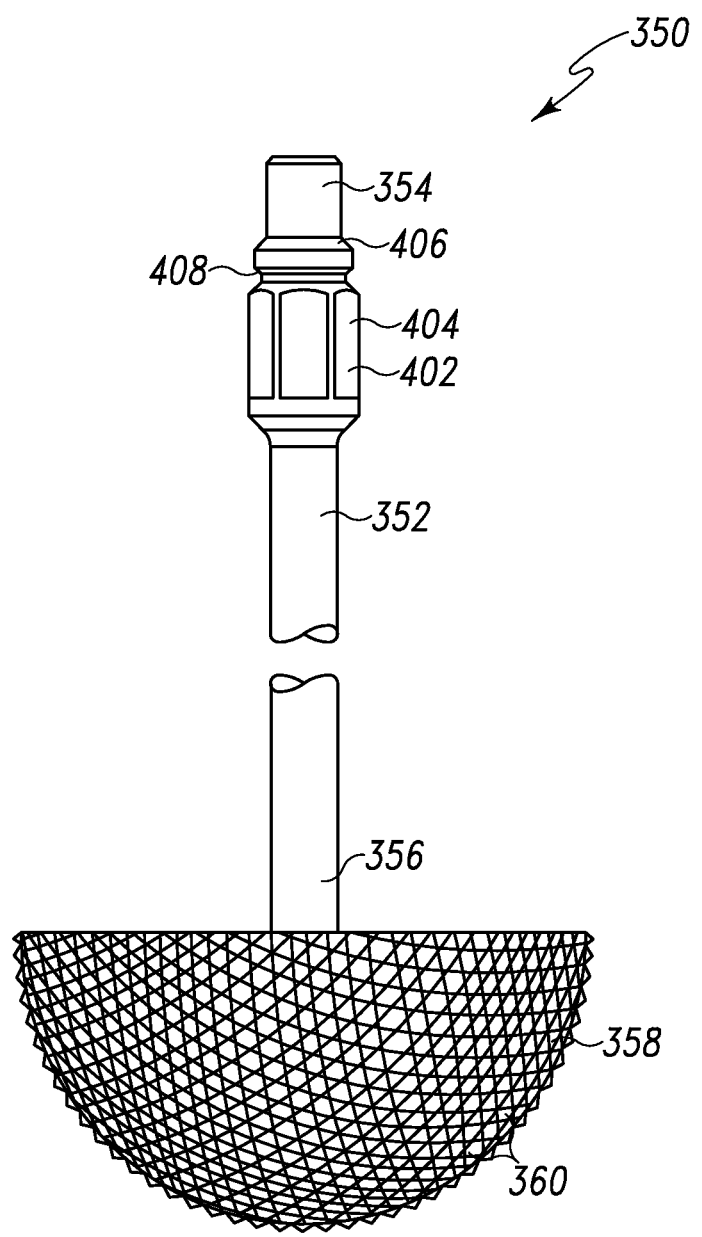
FIG. 39 is a view similar to FIG. 35, but showing another coupling mechanism for coupling the rasp to a hand tool or power tool.
Figure 40:
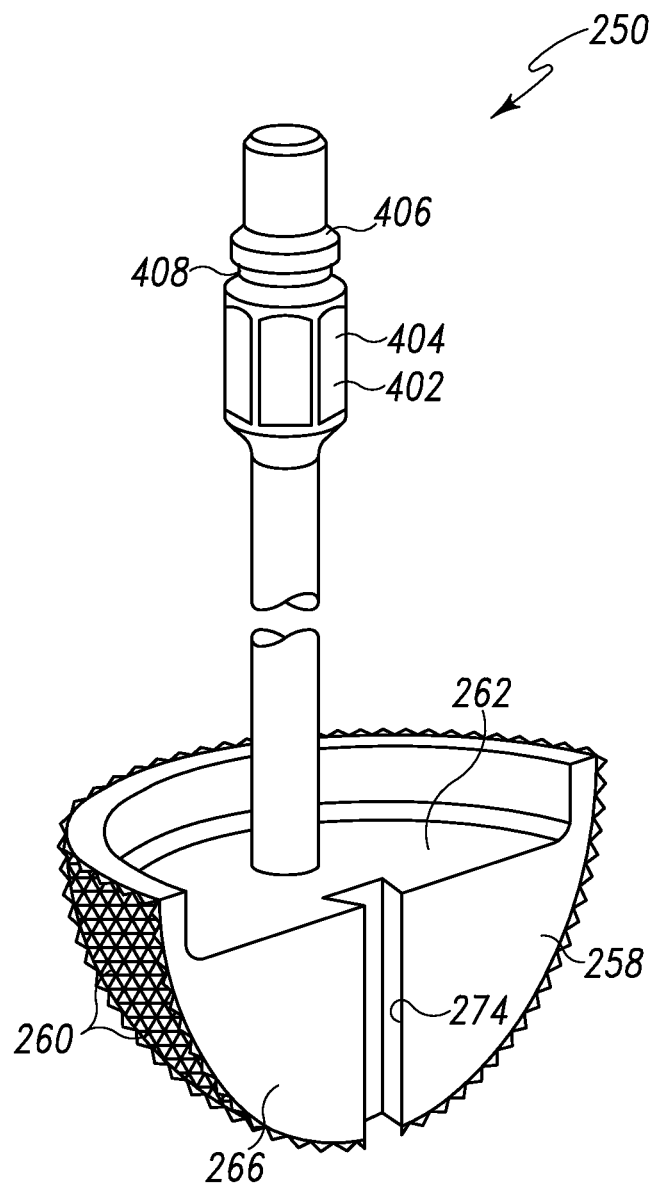
FIG. 40 is a view similar to FIG. 21, but showing another coupling mechanism for coupling the rasp to a hand tool or power tool.
Figure 41:
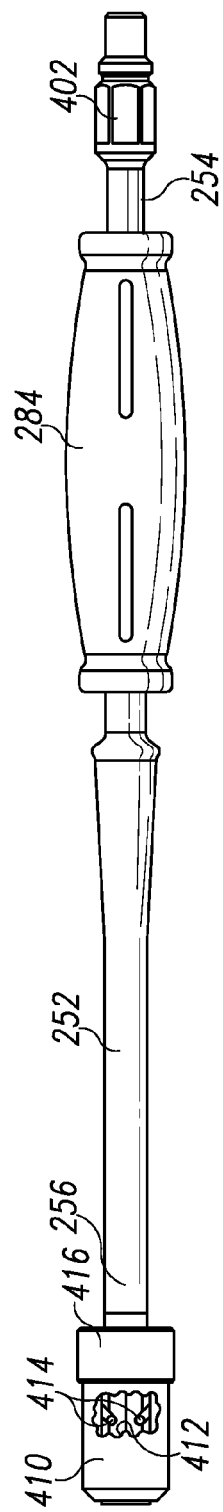
FIG. 41 is a side elevation view of another embodiment of a hand tool.
Figure 42:
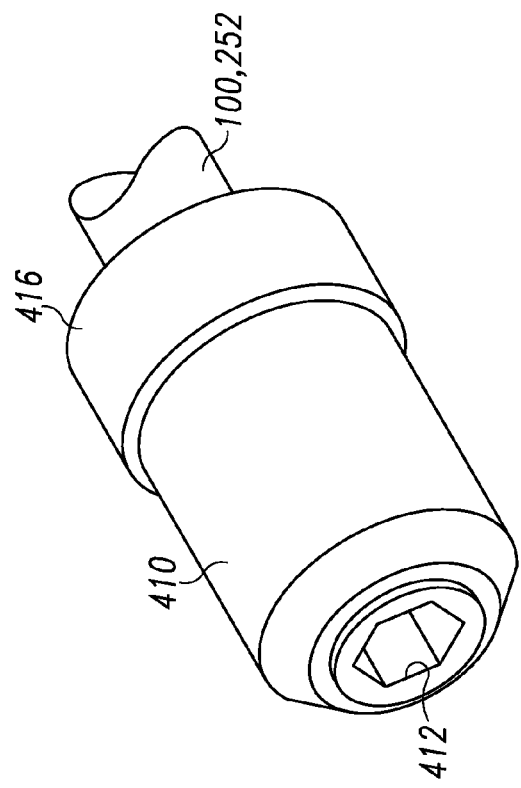
FIG. 42 is a fragmentary perspective view of a female connector that may be used as the chuck of a hand tool or power tool.

Referring now to FIGS. 39-40, there is shown a coupling mechanism that may be used to couple the reciprocating rasps to a hand tool (e.g., a removable shaft such as shown in FIG. 41) or a power tool (e.g., the reciprocating power tool 100). For example, as shown in FIG. 39, the shaft 352 of the reciprocating rasp 350 may be embodied with a male connector 402. The male connector 402 includes a hex-shaped body 404 that is separated from a tapered lead-in surface 406 by an annular channel 408. The male connector 402 mates with a female connector 410 (see FIGS. 41 and 42). As shown in FIG. 41, the female connector 410 may be secured to the end of the removable shaft 352. Alternatively, the female connector 410 may form the chuck of the reciprocating power tool 100.

The female connector 410 includes a hex-shaped cavity 412 that is sized to be slightly larger than the hex-shaped body 404 of the male connector 402. As such, the hex-shaped body 404 of the male connector 402 may be received into the hex-shaped cavity 412 of the female connector 410. As shown in FIG. 41, the female connector 410 also includes a number of spring-loaded jaws 414 positioned in the hex-shaped cavity 412. The jaws 414 are spring biased inwardly toward one another.

To couple the reciprocating rasp 350 to the female connector 410, the free end of the male connector 402 is inserted into the hex-shaped cavity 412 of the female connector 410 with its sides aligned with the sides of the cavity. As the male connector 402 is inserted, the faces of its hex-shaped body 404 align with the faces of the hex-shaped cavity 412 of the female connector 410. The tapered lead-in surface 406 of the male connector 402 forces the spring-loaded jaws 414 away from one another to permit the male connector 402 to fully seat in the female connector 410. Once the jaws 414 have cleared the tapered lead-in surface 406, the spring-loaded jaws 414 are urged toward one another into the annular channel 408 thereby locking the male connector 402 to the female connector 410.

The female connector 410 also includes a sliding collar 416 that is operable to release the male connector 402. In particular, when a surgeon slides the collar 416 away from the rasp 350 (e.g., in a direction toward the handle of the removable shaft of FIG. 41), the spring-loaded jaws 414 are urged away from one another and out of the annular channel 408 of the male connector 402. This unlocks the rasp 350 and allows it to be pulled out of the female connector 410.

As shown in FIG. 40, the cutting head 258 of the reciprocating rasp 250 may be secured to the distal end 256 of a removable shaft 252 by use of the same type of male connector 402. As such, it may also be secured to the chuck of a reciprocating power tool 100 that is equipped with the female connector 410.

As shown in FIG. 41, the proximal end 254 of the removable shaft 252 may be embodied to include a male connector 402. In such a way, it may be secured to the chuck of the reciprocating power tool 100 that includes a female connector 410. In such a configuration, the removable shaft 252 may function as both a hand tool and an extension for securing one of the rasps 250, 350 to the reciprocating power tool 100. Because both the hand tool (i.e., the removable shaft 252) and the chuck of the reciprocating power tool 100 utilize the same female connector 410, the rasps 250, 350 equipped with the male connector 402 may be interchangeably coupled to either tool.

Another embodiment of a female connector 510 for coupling the rasps described herein is shown in FIGS. 43-45. The female connector 510 may be secured to the end of the removable shaft 352, alternatively, the female connector 510 may form the chuck of the reciprocating power tool 100. Like the female connector 410 described above, the female connector 510 includes a hex-shaped cavity 512 that is sized to be slightly larger than the hex-shaped body 404 of the male connector 402. As such, the hex-shaped body 404 of the male connector 402 may be received into the hex-shaped cavity 512 of the female connector 510. As shown in FIGS. 43-45, the female connector 510 includes a spring-loaded button 514. The end 516 of the button 514 extending into the hex-shaped cavity 512 includes a teardrop-shaped opening 518.

To couple one of the reciprocating rasps to the female connector 510, the free end of the male connector 402 is inserted into the hex-shaped cavity 512 of the female connector 510 with its sides aligned with the sides of the cavity. As the male connector 402 is inserted, the faces of its hex-shaped body 404 align with the faces of the hex-shaped cavity 512 of the female connector 510. The tapered lead-in surface 406 of the male connector 402 forces the spring-loaded button 514 downwardly (as viewed in the perspective of FIGS. 44 and 45) to permit the male connector 402 to fully seat in the female connector 510. Once the center of the spring-loaded button 514 has cleared the tapered lead-in surface 406, the spring-loaded button 514 is urged upwardly (as viewed in the perspective of FIGS. 44 and 45) such that a locking flange 520 of the button is received into the annular channel 408 thereby locking the male connector 402 to the female connector 510.

The spring-loaded button 514 is operable to release the male connector 402. In particular, when a surgeon pushes the outer surface 522 of the spring-loaded button 514, the locking flange 520 of the button 514 is urged downwardly (as viewed in the perspective of FIGS. 44 and 45) and out of the annular channel 408 of the male connector 402. This unlocks the rasp and allows it to be pulled out of the female connector 510.

Referring now to FIGS. 46-49 there is shown a spacer block 550 that may be used with the reciprocating rasp 250. The spacer block 550 is used to reduce the number of different rasps 250 that are required to complete a surgical procedure. In particular, the spacer block 550 may be used in lieu of a number of progressively larger-sized cutting heads 258 to produce the desired final size. For example, initial rasping may be performed with a 50 mm cutting head 258 (i.e., a cutting head with a 50 mm OD). Thereafter, instead of replacing the 50 mm cutting head 258 with a larger one to perform a subsequent rasping, the spacer block 550 may be installed on the trial instrument 276 and the 50 mm cutting head 258 used again to make a larger cavity.

Like the surgical rasp 250 and the trial instrument 276, the spacer block 550 also includes alignment guides in the form of members or features that, as will be discussed below in greater detail, align the rasp 250 during a surgical procedure. The alignment member or feature may be embodied as any of numerous different structures or features which are configured to coordinate with the trial instrument 276 to position the cutting head 258 of the rasp 250 in a desired location relative to the trial instrument. Examples of structures that may function as the alignment member include one or more grooves, tracks, sleeves, rings, cannulated bosses, cylinders, guides, hooks, or any other similar structure capable of receiving a complementary structure or feature formed on the trial instrument.

Figure 46:
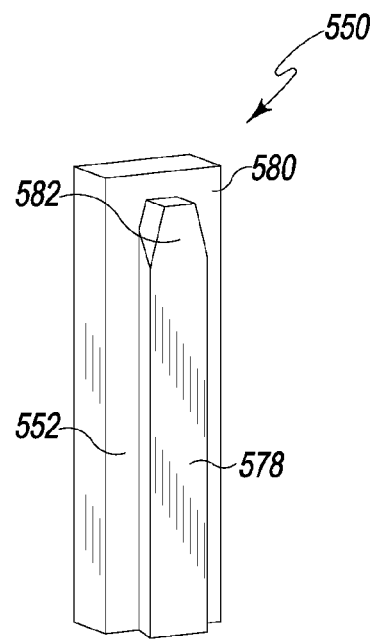
FIG. 46 is a perspective view of a spacer block for use with the reciprocating rasp during rasping of the patient's acetabulum.
Figure 49:
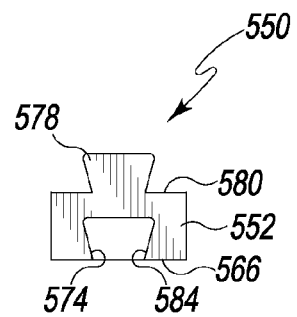
FIG. 49 is a bottom elevation view of the spacer block of FIG. 46.

In the illustrative embodiment described herein, the spacer block 550 has an elongated groove 574 formed in the posterior surface 566 (see FIGS. 47 and 49) of its body 552. As can be seen in FIGS. 46 and 49, the spacer block 550 includes an elongated tongue 578 formed in the anterior surface 580 of its body 552. During rasping of the patient's acetabulum, the groove 574 of the spacer block 550 is received into the tongue 278 of the trial instrument 276, and the tongue 578 of the spacer block 550 is positioned in the groove 274 of the rasp 250 thereby establishing and maintaining the alignment of the rasp.

Figure 48:
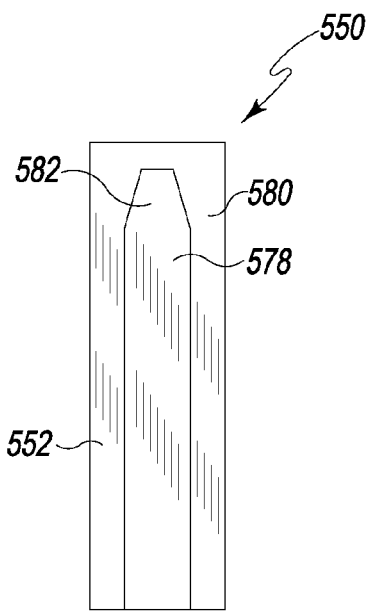
FIG. 48 is a front elevation view of the spacer block of FIG. 46.

As can be seen in FIGS. 46 and 48, the elongated tongue 578 of the spacer block has a tapered tip 582. The tapered tip 582 eases insertion of the elongated tongue 578 into the elongated groove 274 of the rasp 250. It should be appreciated that the elongated tongue 278 of the trial instrument 276 may be embodied with such a tapered tip 582.

Figure 47:
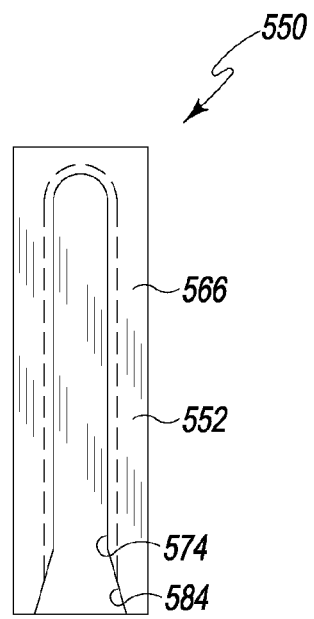
FIG. 47 is a rear elevation view of the spacer block of FIG. 46.
Figure 50:
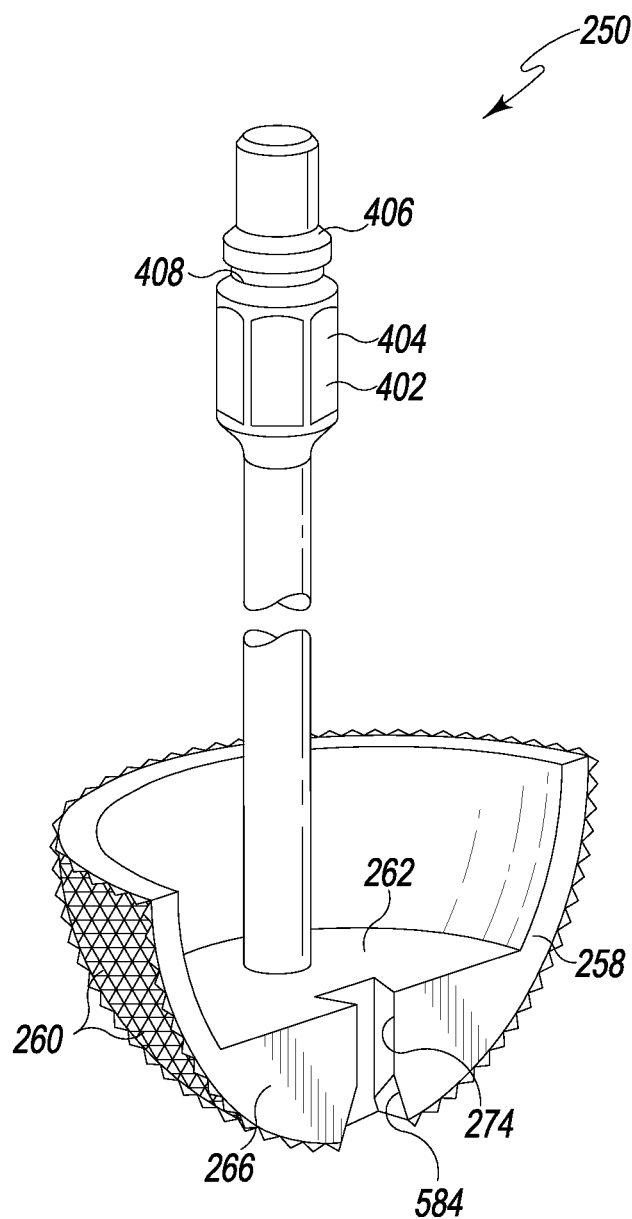
FIG. 50 is a view similar to FIG. 40, but showing the reciprocating rasp having an elongated groove with a flared open end.

As shown in FIG. 47, the elongated groove 574 has a flared open end 584. Like the tapered tip 582 of the elongated tongue 578, the flared open end 584 eases insertion of the elongated tongue 278 of the trial instrument 276 into the elongated groove 574. As shown in FIG. 50, the cutting head 256 of the rasp 250 may be embodied with such a flared open end 584.

The spacer block 550 may be provided in numerous different thicknesses to facilitate progressive rasping in different sizes. It should also be appreciated that multiple spacer blocks 550 may be used at the same time to create different rasping sizes.

Figure 51:
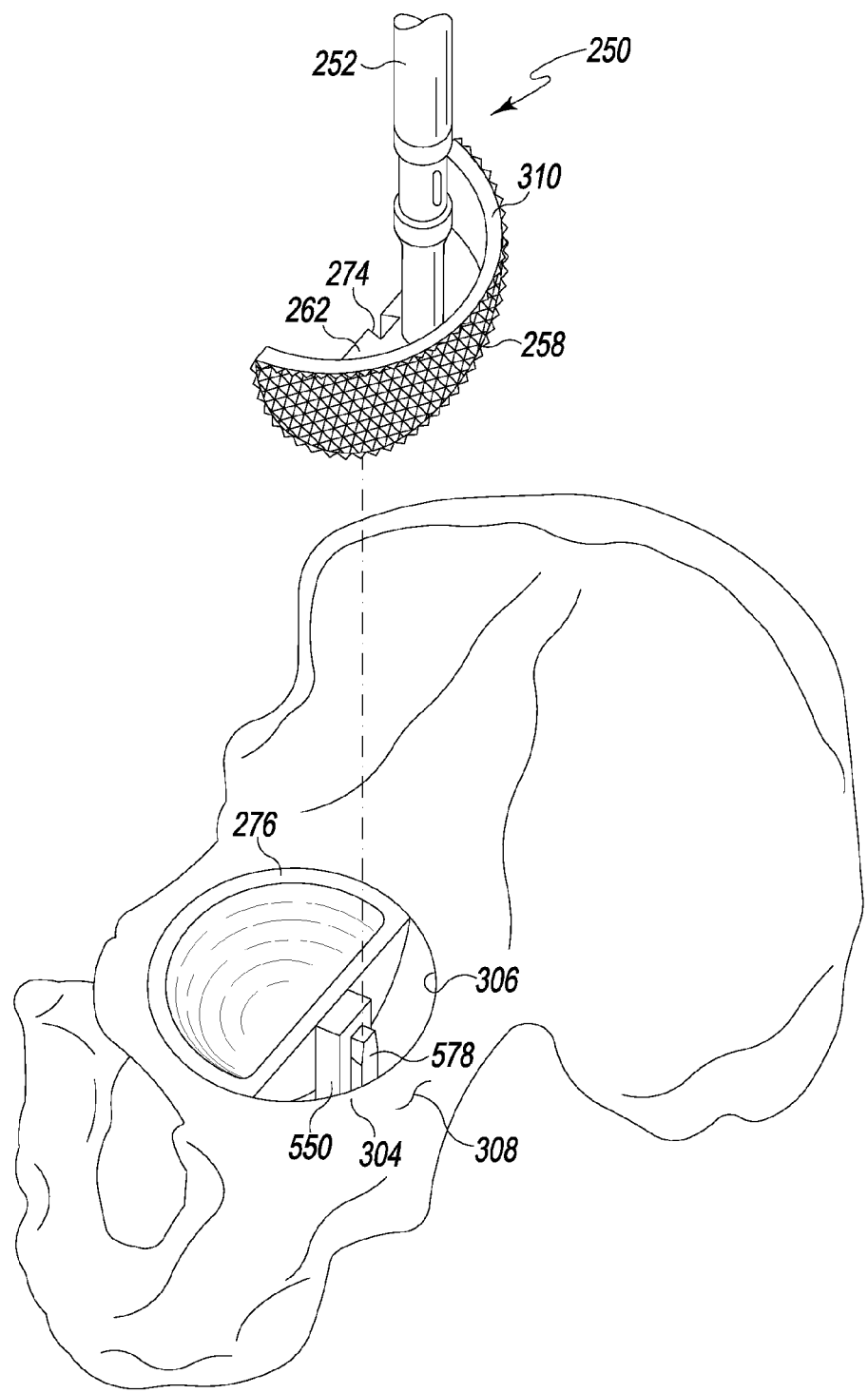
FIGS. 51 and 52 are views similar to FIG. 29 showing the reciprocating rasp during rasping of the patient's acetabulum with the use of the spacer block of FIGS. 46-49.
Figure 52:
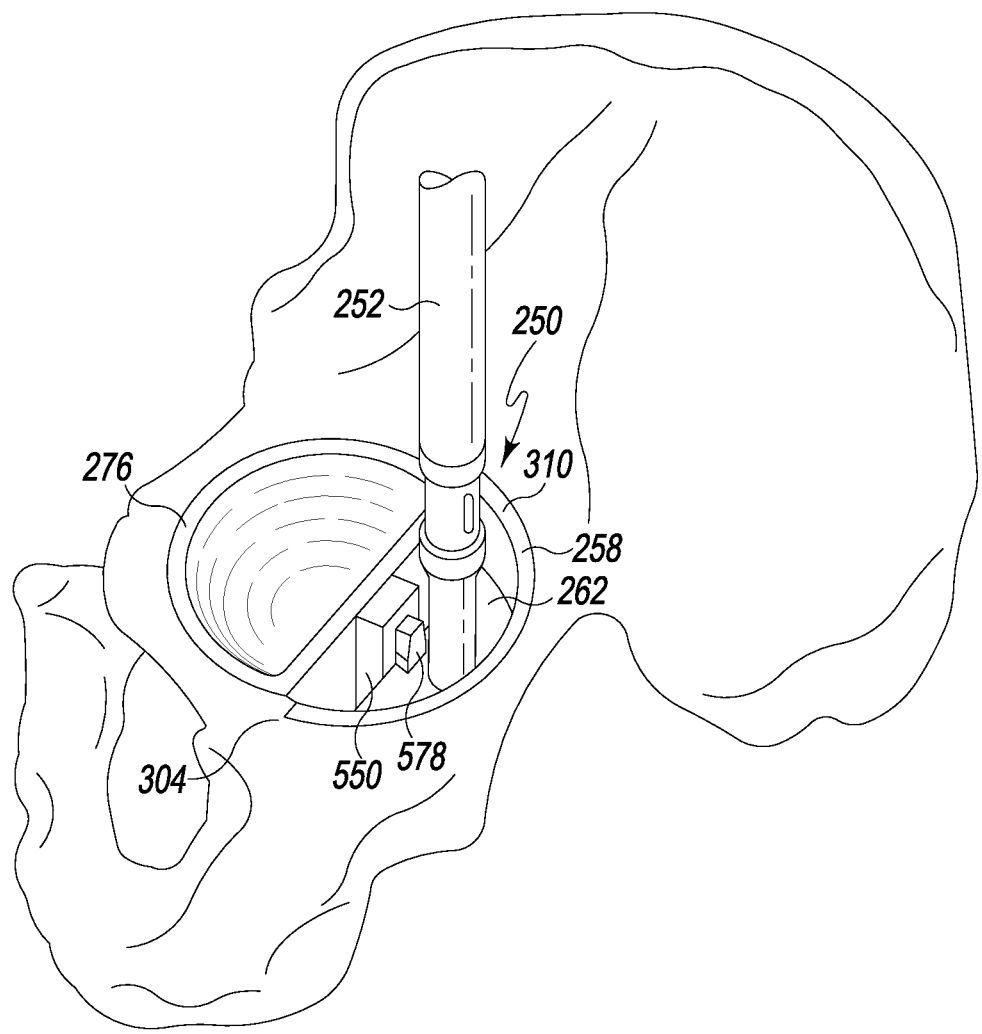

Referring now to FIGS. 51 and 52, there is shown a surgical procedure using the spacer block 550. As shown in FIG. 51, the reciprocating rasp 250 is being used to remove the diseased or deteriorated bone tissue 308 of the hip bone. The spacer block 550 has been installed on the trial instrument 276. In particular, the spacer block 550 has been positioned such that the tongue 278 of the trial instrument 276 has been inserted into the groove 574 of the spacer block 550 thereby securing the spacer block 550 to the trial instrument 276. With the appropriate cutting head 258 coupled to the shaft 252, the surgeon then advances the rasp 250 toward the trial instrument 276 positioned in the reamed surface 306. The surgeon positions the rasp 250 such that the elongated tongue 578 formed in the anterior surface 580 of the spacer block 550 is received into the groove 274 of the cutting head 258 thereby establishing and maintaining alignment of the rasp 250 relative to the trial instrument 276.

Once the elongated tongue 578 of the spacer block 550 is received into the groove 274 of the cutting head 258, the surgeon activates the reciprocating power tool 100 (if the rasp 250 is being powered by the power tool 100 as opposed to manual operation of the shaft 252 via its handle 284) and advances the lead cutting surface of the cutting head 258 into contact with the patient's acetabulum 304. As shown in FIG. 52, as the rasp 250 is advanced inwardly toward the patient's acetabulum 304, the reciprocating motion of the rasp 250 abrades the bone and continues to remove bone until the upper edge 310 of the lateral surface 262 of the cutting head 258 is substantially flush with the bone of the patient's acetabulum 304 remaining outside of the rasped surface (i.e., the bone of the acetabulum that is not intended to be removed by the rasp 250). When the upper edge 310 of the lateral surface 262 of the cutting head 258 is flush with the remaining bone in such a manner, the rasping preparation of the acetabulum 304 with that particular cutting head 258 is complete.

The surgeon may then install another spacer block 550 on the existing spacer block and rasp the bone a subsequent time. Alternatively, the surgeon may swap the spacer block 550 for a larger one. Yet further, the surgeon may use a larger cutting head 256 with or without a spacer block 550.

It should be appreciated that the coupling mechanisms described herein are merely exemplary in nature. It is contemplated that numerous different types of coupling mechanisms may be used with the reciprocating rasps described herein. Moreover, modifications of the coupling mechanisms described herein are also contemplated. For example, the male connector 402 may be used in the design of a hand tool or chuck of a power tool with the rasp having a corresponding female connector 410.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A reciprocating rasp surgical instrument for use in the surgical preparation of an acetabulum of a patient prior to implantation of a prosthetic acetabular component, the reciprocating rasp comprising:
    a shaft having a first end configured to be secured in a chuck of a reciprocating tool, and
    a cutting head secured to a second end of the shaft, the cutting head comprising (i) a cutting surface having a plurality of cutting teeth arranged in a geometry that corresponds with a geometry of the acetabular component, and (ii) an alignment guide that is devoid of cutting teeth and configured to cooperate with a complementary alignment guide of an acetabular trial instrument when the cutting head is secured to the second end of the shaft, wherein the cutting head is half-hemispherically shaped and comprises (i) a lateral surface, (ii) a posterior surface extending medially from the lateral surface, both the lateral surface and the posterior surface being devoid of cutting teeth, and (iii) a curved medial cutting surface that mates with both the lateral surface and the posterior surface, and the alignment guide comprises an elongated groove formed in the posterior surface of the cutting head.

2. The reciprocating rasp surgical instrument of claim 1, wherein the complementary alignment guide of the acetabular trial instrument includes a tongue, and wherein the elongated groove is configured to receive the tongue of the acetabular trial instrument.

3. The reciprocating rasp surgical instrument of claim 1, wherein the shaft is detachable from the cutting head.

* * * * *